US008758991B2

(12) United States Patent
Klein et al.

(10) Patent No.: US 8,758,991 B2
(45) Date of Patent: Jun. 24, 2014

(54) ISOLATION OF MEMBRANE VESICLES FROM BIOLOGICAL FLUIDS AND METHODS OF USING SAME

(75) Inventors: Jon Klein, Louisville, KY (US); Elias Klein, Louisville, KY (US); Michael Merchant, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 724 days.

(21) Appl. No.: 12/298,467

(22) PCT Filed: Apr. 26, 2007

(86) PCT No.: PCT/US2007/067509
§ 371 (c)(1),
(2), (4) Date: Nov. 7, 2008

(87) PCT Pub. No.: WO2007/127848
PCT Pub. Date: Nov. 8, 2007

(65) Prior Publication Data
US 2009/0258379 A1    Oct. 15, 2009

Related U.S. Application Data

(60) Provisional application No. 60/795,063, filed on Apr. 26, 2006.

(51) Int. Cl.
*C12Q 1/00* (2006.01)
(52) U.S. Cl.
USPC .......................................................... 435/4
(58) Field of Classification Search
USPC .......................................................... 435/4
See application file for complete search history.

(56) References Cited

U.S. PATENT DOCUMENTS

| 5,538,897 | A | 7/1996 | Yates, III et al. | |
| 6,812,023 | B1 * | 11/2004 | Lamparski et al. | 435/325 |
| 6,899,863 | B1 | 5/2005 | Dhellin et al. | |

FOREIGN PATENT DOCUMENTS

WO         99/03499         1/1999

OTHER PUBLICATIONS

Dyer et al. "Glycyl-L-proline transport in rabbit enterocyte basolateral-membrane vesicles", Biochem. 1990, 269:565-571.*
Davidson et al. "Acidic pH requirement for insertion of colicin E1 into artificial membrane vesicles: relevance to the mechanism of action of colicins and certain toxins" Proc. Nat. Acad. Sci., USA, 1985, 82:1386-1390.*
Segura et al. "ICAM-1 on exosomes from mature dendritic cells is critiacl for efficient naïve T-cell priming", Blood, 2005, 106(1):216-223.*
Turner et al. "Multiple components of synaptosomal 3H-gamma-aminobutyric acid release resolved by a rapid superfusion system", Biochemistry, 1989, 28:586-593.*
Millipore membrane filter product sheet: 1 page, from website, captured on Dec. 2007.*
Granicka et al. "Polypropylene silanized membranes for immunoisolation" Separation and Purification Technology, 2005, 41:221-230.*
Sartorius filter information, 2010, pp. 1-18.*
Anderson et al., "Quantitative mass spectrometric MRM assays for major plasma proteins," Mol Cell Proteomics, 5 (4), 2005, pp. 573-588.
Berhane et al., "Cardiovascular-related proteins identified in human plasma by the HUPO Plasma Proteome Project pilot phase," Proteomics, 5(13), 2005, pp. 3520-3530.
Caby et al., "Exosomal-like vesicles are present in human blood plasma," Int Immunol., 17(7), 2005, pp. 879-887.
Cheruvanky et al., "Rapid isolation of urinary exosomal biomarkers using a nanomembrane ultrafiltration concentrator," Am J Phys Renal Physiol., 292, 2007, F1657-F1661.
Echan et al., "Depletion of multiple high-abundance proteins improves protein profiling capacities of human serum and plasma," Proteomics, 5(13), 2005, pp. 3292-3303.
Gatti et al., "Identification, proteomic profiling, and origin of ram epididymal fluid exosome-like vesicles. Gentamicin-induced nephrotoxicity in the rat," Biol Reprod., 72(6), 2005, pp. 1452-1465.
Greenough et al., "A method for the rapid depletion of albumin and immunoglobulin from human plasma," Proteomics, 4(10), 2004, pp. 3107-3111.
Haubitz et al., "Urine protein patterns can serve as diagnostic tools in patients with IgA nephropathy," Kidney Int., Jun;67(6), 2005, pp. 2313-2320.
Hegmans et al., "Proteomic analysis of exosomes secreted by human mesothelioma cells," Am J Pathol., 164(5), 2004, pp. 1807-1815.
Hines et al., "Pattern-based algorithm for peptide sequencing from tandem high energy collision-induced dissociation mass spectra," J. Am. Soc. Mass Spectrom., 3, 1995, pp. 326-336.
Knapp et al., "Peptide sequence determination from high-energy CID spectra using artificial neural networks," Am. Soc. Mass Spectrom., 6, 1995, pp. 947-961.
Lamparski et al., "Production and characterization of clinical grade exosomes derived from dendritic cells," Journal of Immunological Methods, 270, 2002, pp. 211-226.

(Continued)

*Primary Examiner* — Bin Shen
(74) *Attorney, Agent, or Firm* — Stites & Harbison PLLC; Terry L. Wright

(57) ABSTRACT

Methods of isolating membrane vesicles from a biological fluid sample are provided. In some embodiments, the methods comprise providing a biological fluid sample comprising membrane vesicles; filtering the biological fluid sample through a filtration module comprising a filter having an average pore diameter of between about 0.01 um and about 0.15 um; and collecting from the filtration module a retentate comprising the membrane vesicles, thereby isolating the membrane vesicles from the biological fluid sample.

76 Claims, 6 Drawing Sheets

(56) References Cited

OTHER PUBLICATIONS

Lenz et al., "Metabonomics with 1H-NMR spectroscopy and liquid chromatography-mass spectrometry applied to the investigation of metabolic changes caused by gentamicin-induced nephrotoxicity in the rat," Biomarkers, 10(2-3), 2005, pp. 173-187.

Mallegol et al., "Phenotypic and functional characterization of intestinal epithelial exosomes," Blood Cells Mol Dis., 35(1), 2005, pp. 11-16.

Mann et al., "Error-tolerant identification of peptides in sequence databases by peptide sequence tags," Anal Chem., 66(24), 1994, pp. 4390-4399.

Mortz et al., "Sequence tag identification of intact proteins by matching tandem mass spectral data against sequence data bases," Proc Nat Acad Sci USA, 93(16), 1996, pp. 8264-8267.

Patel et al., "An analysis of variability in the manufacturing of dexosomes: implications for development of an autologous therapy," Biotech Bioeng., 92(2), 2005, pp. 238-249.

Snyder et al., "Detection and evaluation of chronic kidney disease," Am Fam Physician, 72(9), 2005, pp. 1723-1732.

Thongboonkerd et al., "Proteomic analysis of normal human urinary proteins isolated by acetone precipitation or ultracentrifugation," Kidney Int., 62(4), 2002, pp. 1461-1469.

Veenstra et al., "Biomarkers: mining the biofluid proteome," Mol Cell Proteomics, 4(4), 2005, pp. 409-418.

Vidal et al., "Towards the application of proteomics in renal disease diagnosis," Clin Sci (Lond),109(5), 2005, pp. 421-430.

Zhou et al., "An investigation into the human serum "interactome"," Electrophoresis, 25(9), 2004, pp. 1289-1298.

Zhou et al., "Exosomal Fetuin-A identified by proteomics: A novel urinary biomarker for detecting acute kidney injury," Kidney International, 70, 2006, pp. 1847-1857.

Pisitkun et al., "Identification and proteomic profiling of exosomes in human urine," PNAS, 101(36), 2004, pp. 13368-13373.

Hoorn et al., "Prospects for urinary proteomics: exosomes as a source of urinary biomarkers," Nephrology, 10, 2005, pp. 283-290.

Zhou et al., "Collection, storage, preservation, and normalization of human urinary exosomes for biomaker discovery," Kidney International, 69, 2006, pp. 1471-1476.

ISA/US, International Search Report and Written Opinion for international application No. PCT/US07/67509, mailed Oct. 1, 2007.

Thery et al., "Proteomic Analysis of Dendritic Cell-Derived Exosomes: A Secreted Subcellular Compartment Distinct from Apoptotic Vesicles," J Immunol, 2001, vol. 166, pp. 7309-7318.

* cited by examiner ically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

ISOLATION OF MEMBRANE VESICLES FROM BIOLOGICAL FLUIDS AND METHODS OF USING SAME

RELATED APPLICATIONS

The presently disclosed subject matter claims the benefit of U.S. Provisional Patent Application Ser. No. 60/795,063, filed Apr. 26, 2006; the disclosure of which is incorporated herein by reference in its entirety.

TECHNICAL FIELD

The presently disclosed subject matter relates to isolating membrane vesicles from biological fluids. In particular, the presently disclosed subject matter relates to isolating membrane vesicles and membrane vesicle-associated polypeptides from biological fluids for identification and/or quantitation of the polypeptides.

BACKGROUND

Analyses of the human proteome hold the promise of the ability for early identification of disease and for insights into the pathological processes involved (Berhane et al., 2005; Zhao et al., 2005; Veenstra et al., 2005). A difficult problem associated with this goal is the need to sample the proteins involved easily and to do so over a wide dynamic range (Anderson & Hunter, 2005; Vidal et al., 2005). For screening large populations, urine and plasma provide a convenient access to fluids equilibrated with total body metabolism. However, each of these sources presents unique problem sets in sample preparation.

Plasma contains high concentrations of both albumin and IgGs so that the detection and identification of non-(Alb+ IgG) proteins is made difficult if the highly predominant species are not selectively removed. Affinity methods for their reduction in intact or diluted plasma have been reported (Echan et al., 2005; Greenough et al., 2004), but this removal may be accompanied by loss of peptides or other metabolites complexed to the highly abundant species (Zhou et al., 2004). Despite this problem, plasma offers a rich and relatively constant concentration of proteins in a milieu suitable for various analytical methods used in proteomic analysis.

Urine also provides a simple access to body fluids, but the analytical difficulties are quite different than plasma (Haubitz et al., 2005). Urine has temporal variations in urine protein, peptide, and metabolomic content that must be overcome by sampling pooled collections (Lenz et al., 2005). Excluding breach of the glomerular filtration unit, protein concentrations are generally much lower than in plasma and can be accompanied by highly variable electrolyte levels so that simple concentration without electrolyte separation is not indicated. More recently, the presence of hydrophobic, membrane proteins (Thongboonkerd et al., 2002), whose source has been traced to urinary exosomes (Pisitkun et al., 2004), has opened the possibility of preliminary separation of these particles from high molecular weight, but soluble, proteins and both of these from low molecular weight proteins and peptides.

Thus, there is an unmet need in the art for improved methods of isolating polypeptides from biological fluids for proteomic analysis. Further, there is an unmet need for improved methods of isolating exosomes from biological fluids, wherein the exosomes comprise a useful subset of biomarker polypeptides having applications in proteomic analysis generally and disease diagnosis and progression in particular.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In one embodiment of the presently disclosed matter, a method of isolating membrane vesicles from a biological fluid sample is provided. In some embodiments, the method comprises providing a biological fluid sample comprising membrane vesicles; filtering the biological fluid sample through a filtration module comprising a filter having an average pore diameter of between about 0.01 μm and about 0.15 μm; and collecting from the filtration module a retentate comprising the membrane vesicles, thereby isolating the membrane vesicles from the biological fluid sample.

In another embodiment of the presently disclosed subject matter, a method of identifying biomarker polypeptides and/ or quantitating biomarker polypeptides in a biological fluid sample is provided. In some embodiments, the method comprises providing a biological fluid sample comprising membrane vesicles, wherein the membrane vesicles comprise biomarker polypeptides; filtering the biological fluid sample through a filtration module comprising a filter having an average pore diameter of between about 0.01 um and about 0.15 um; collecting from the filtration module a retentate comprising the membrane vesicles; isolating the biomarker polypeptides from the membrane vesicles; and identifying and/or quantitating the isolated biomarker polypeptides.

In still another embodiment of the presently disclosed subject matter, a method of isolating membrane vesicle biomarker polypeptides from a biological fluid sample is provided. In some embodiments, the method comprises providing a biological fluid sample comprising membrane vesicles, wherein the membrane vesicles comprise biomarker polypeptides; filtering the biological fluid sample through a filtration module comprising a filter having an average pore diameter of between about 0.01 um and about 0.15 um; collecting from the filtration module a retentate comprising the membrane vesicles; and isolating the biomarker polypeptides from the membrane vesicles. In some embodiments, the biomarker peptides are isolated by electrophoretic separation, immunoisolation, chromatography, or combinations thereof.

In still another embodiment of the presently disclosed subject matter, a method of diagnosing a disorder or measuring a disorder state in a subject is provided. In some embodiments, the method comprises providing a biological fluid sample comprising membrane vesicles, wherein the membrane vesicles comprise biomarker polypeptides; filtering the biological fluid sample through a filtration module comprising a filter having an average pore diameter of between about 0.01 um and about 0.15 um; collecting from the filtration module a retentate comprising the membrane vesicles; isolating the biomarker polypeptides from the membrane vesicles; and identifying, quantitating, or both the isolated biomarker polypeptides, wherein the identified and/or quantitated biomarker polypeptides indicates the presence of a disorder or is a measure of a disorder state in the subject. In some embodiments of the diagnostic method, the disorder is selected from the group consisting of diabetes, water-balance disorders, acute kidney injury, glomerulonephritis, drug-induced acute renal failure and allergy, acute and chronic kidney transplant rejection, inherited renal diseases, myocardial ischemia, cardiovascular risk, prostatic hypertrophy and prostatic cancer, systemic lupus erythematosus, and rheumatoid arthritis.

In some embodiments of the methods disclosed herein, the biological fluid sample provided is a clarified biological fluid sample, such as for example by low-speed centrifugation (e.g., 3,000×g or less) and collection of a supernatant comprising the clarified biological fluid sample. In some embodiments, the biological fluid sample is selected from the group consisting of blood, blood plasma, and urine. In some embodiments, the biological fluid sample is urine, which is treated with a protease inhibitor.

In some embodiments of the methods disclosed herein, the membrane vesicles are exosomes. In some particular embodiments, the exosomes are urinary exosomes. In some embodiments, the retentate comprising the membrane vesicles is collected by washing the retentate from the filtration module. Further, in some embodiments, the collected retentate is resuspended in a buffer solution.

In some embodiments of the methods disclosed herein, the filtration module is a fiber-based filtration cartridge, which can in some embodiments include a filter comprising polypropylene hollow fibers. In some embodiments, the filtration module is a membrane filtration module, which can in some embodiments include a filter comprising a filtration disc composed of hydrophilic polyvinylidene difluoride. In some embodiments, the filter has an average pore diameter of about 0.1 µm. In some embodiments, the filter comprises a material selected from the group consisting of polypropylene, polyvinylidene difluoride, polyethylene, polyfluoroethylene, cellulose, secondary cellulose acetate, polysulfone and polyethersulfone, polyvinylalcohol and ethylenevinyl alcohol.

In some embodiments of the methods, the biomarker peptides are identified, quantitated, or both by immunoassay, mass spectrometry, or both. In some embodiments, the mass spectrometry is matrix-assisted laser desorption ionization time-of-flight mass spectrometry (MALDI MS). In some embodiments, the biomarker polypeptides are separated by liquid chromatography (LC) methods. In some embodiments the biomarker polypeptides are analyzed in line with LC methods using electrospray ionization (ESI) MS methods. In some embodiments the biomarker polypeptides are analyzed directly or off line by LC methods using matrix-assisted laser desorption ionization time-of-flight mass spectrometry (MALDI MS). Further, in some embodiments, the immunoassay is selected from the group consisting of Western blot, enzyme-linked immunoassay (ELISA), radioimmunoassay (RIA), and competitive binding assay.

Accordingly, it is an object of the presently disclosed subject matter to isolate membrane vesicles from biological fluids. This object is achieved in whole or in part by the presently disclosed subject matter.

An object of the presently disclosed subject matter having been stated hereinabove, and which is achieved in whole or in part by the presently disclosed subject matter, other objects and advantages will become evident to those of ordinary skill in the art after a study of the following description of the presently disclosed subject matter, [DRAWINGS?], and non-limiting examples.

DETAILED DESCRIPTION

Figure 1:
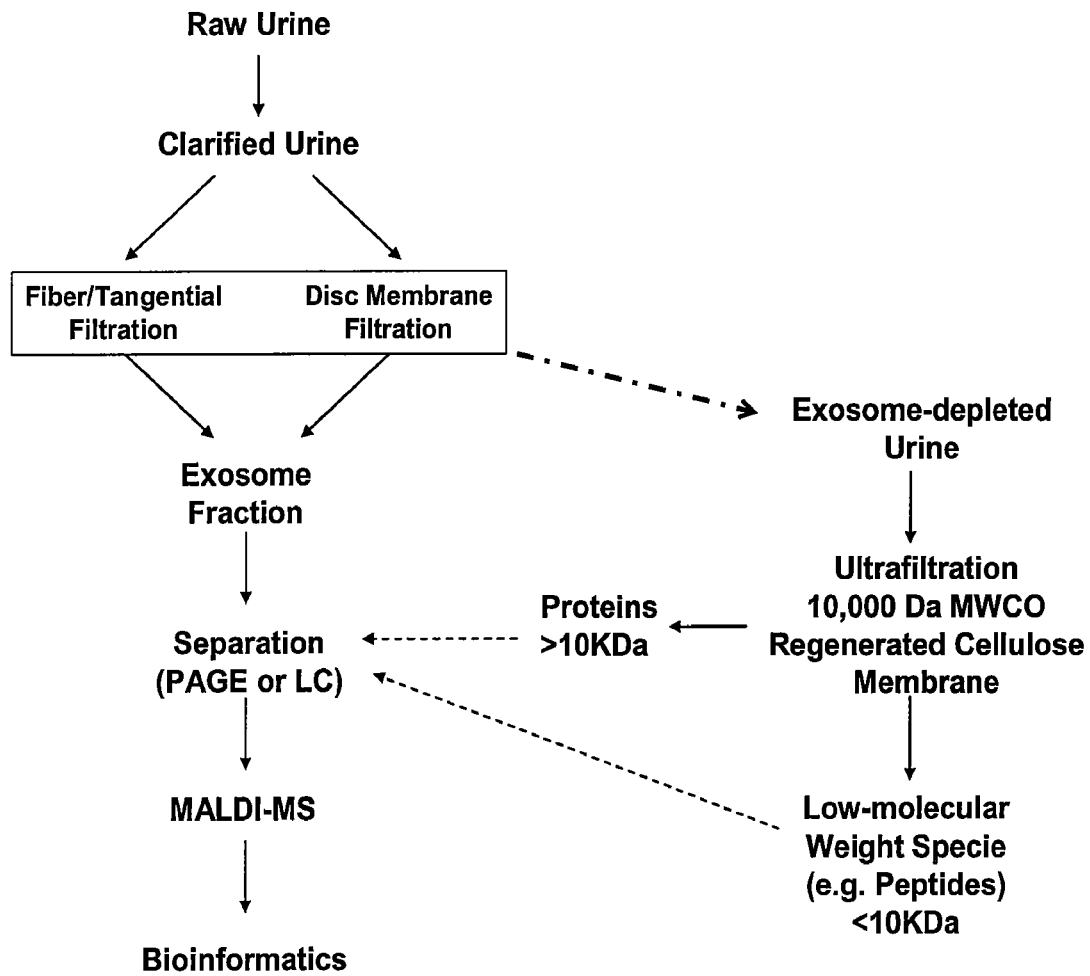
FIG. 1 is a schematic drawing showing sample handling and workflow.

The details of one or more embodiments of the presently disclosed subject matter are set forth in the accompanying description below. Other features, objects, and advantages of the presently disclosed subject matter will be apparent from the detailed description, figures, and claims. All publications, patent applications, patents, and other references disclosed herein are incorporated by reference in their entirety. Some of the polypeptides disclosed herein are cross-referenced to public database accession numbers. The complete sequences cross-referenced in the database are expressly incorporated by reference as are equivalent and related sequences present in other public databases. Also expressly incorporated herein by reference are all annotations present in the database associated with the sequences disclosed herein. In case of conflict, the present specification, including definitions, will control. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments 10%, in some embodiments ±5%, in some embodiments ±1%, in some embodiments ±0.5%, and in some embodiments ±0.1% from the specified amount, as such variations are appropriate to perform the disclosed method.

Biological fluids are valuable as indicators of a subject's well-being and can be analyzed for data indicative of the presence or absence and progression of disease. For example, urine is one biological fluid that has clinical diagnostic value (Snyder & Pendergraph, 2005). In addition to low molecular weight species like glucose, bilirubin, ketones, sodium, potassium, and nitrites, urine contains specific proteins and peptides that have significant diagnostic value. One problem with the development of diagnostic protein or peptide markers (biomarkers) is the relative (low) concentration of the species that is sensitive and specific for a given disease; especially for the detection of a disease in the pre-pathologic state.

Considerable effort has been applied toward pre-fractionation of biological fluid samples with the goal of increasing the relative concentration of all peptide species in a given sample fraction (Anderson & Hunter, 2005; Vidal et al., 2005). Certain tissues through normal biological processes produce membrane vesicles containing a variety of polypeptides. In certain disease states, particular systems, such as for example the immune system can increase production of membrane vesicles.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long.

A fragment can retain one or more of the biological activities or diagnostic characteristics of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived.

The term "membrane vesicle" as used herein refers to essentially spherical vesicles, generally less than about 130 nm in diameter, comprising of a lipid bilayer containing a cytosolic fraction and secreted from cells. Particular membrane vesicles are more specifically produced by cells, from intracellular compartments through fusion with the plasma membrane of a cell, resulting in their release in biological fluids or in the supernatant of cells in culture. Such vesicles are generally referred to as exosomes. Exosomes can be between about 30 and about 120 nm, and more specifically between about 50 and 90 nm in diameter and, advantageously, carry membrane proteins. In addition, depending on their origin, exosomes comprise membrane proteins such as for example MHC I, MHC II, CD63, CD81 and/or HSP70 and have no endoplasmic reticulum or Golgi apparatus. Furthermore, exosomes are typically devoid of nucleic acids (e.g., DNA or RNA).

Exosome release has been demonstrated from different cell types in varied physiological contexts. For example, it has been demonstrated that B lymphocytes release exosomes carrying class II major histocompatibility complex molecules, which play a role in antigenic presentation. Similarly, it has been demonstrated that dendritic cells produce exosomes (i.e., "dexosomes" or "Dex"), with specific structural and functional characteristics and playing a role in immune response mediation, particularly in cytotoxic T lymphocyte stimulation. It has also been demonstrated that tumor cells secrete specific exosomes (i.e., "texosomes" or "Tex") in a regulated manner, carrying tumor antigens and capable of presenting these antigens or transmitting them to antigen presenting cells (see e.g., PCT International Patent Application No. WO99/03499, herein incorporated by reference in its entirety). Also, mastocyte cells accumulate molecules in intracellular vesicular compartments, which can be secreted under the effect of signals. The kidneys also produce exosomes (i.e., urinary exosomes) (Pisitkun et al., 2004).

Therefore, as a general rule, cells appear to emit signals and communicate with each other via membrane vesicles that they release, which may carry proteins or any other signal with specific structural and functional characteristics, produced in different physiological situations. The exosome in effect is the end result of a pre-fractionation process by tissues. The vesicles are then delivered to various biological fluids, including for example blood and urine. As such, disease biology might produce a diagnostic species in increased concentration localized in membrane vesicles, including for example exosomes. Therefore membrane vesicles have value as polypeptide biomarker reservoirs and efforts to simplify the purification of membrane vesicles (e.g., exosomes) from biological fluids, including blood and urine, have diagnostic and health assessment value.

Accordingly, the presently disclosed subject matter provides methods of isolating membrane vesicles from biological samples. In some embodiments, the methods comprise providing a biological fluid sample comprising membrane vesicles; filtering the biological fluid sample through a filtration module comprising a filter having an average pore diameter of between about 0.01 μm and about 0.15 μm; and collecting from the filtration module a retentate comprising the membrane vesicles, thereby isolating the membrane vesicles from the biological fluid sample. In some embodiments, the biological sample can be treated at some point after sample collection with one or more protease inhibitors to prevent degradation of the proteins in the biological sample prior to isolation (e.g., serine protease inhibitors, chymotrypsin inhibitors, trypsin inhibitors, etc.).

The term "isolated", when applied to a nucleic acid or polypeptide, denotes that the nucleic acid or polypeptide is essentially free of other cellular components with which it is associated in the natural state. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A polypeptide that is the predominant species present in a preparation is substantially isolated. The term "isolated" denotes that a nucleic acid or polypeptide gives rise to essentially one band in an electrophoretic gel. Particularly, it means that the nucleic acid or polypeptide is in some embodiments at least about 50% pure, in some embodiments at least about 85% pure, and in some embodiments at least about 90%, 95%, 96%, 97%, 98% or 99% pure.

As demonstrated in the present Examples, the presently disclosed methods can be used to isolate membrane vesicles that maintain the presence of peripheral and integral membrane proteins, as well as globular membrane proteins. The presence of globular membrane proteins is indicative of the maintenance of the membrane vesicle structure, and little to no loss of vesicle contents.

The term "biological sample" as used herein refers to a sample that comprises a biomolecule and/or is derived from a subject. The biological sample can be utilized for the detection of the presence and/or quantitative level of a polypeptide of interest. Representative biomolecules include, but are not limited to DNA, RNA, mRNA, and polypeptides. As such, a biological sample can comprise a cell, a group of cells, fragments of cells, or cell products, including for example membrane vesicles (e.g., exosomes). Any cell, group of cells, cell fragment, or cell product can be used with the methods of the presently claimed subject matter, although cell-types and organs that would be predicted to show differential gene and/or polypeptide expression in subjects with disorders versus normal subjects are best suited. In some embodiments, the biological fluid can be blood, blood plasma, cerebrospinal fluid, saliva, tears, alveolar isolates, pleural fluid, pericardial fluid, bile, pancreatic exocrine fluid, ascites, cyst fluid and/or urine In embodiments of the presently disclosed subject matter where the biological fluid is urine, the urine can be freshly collected or previously frozen urine. Additionally, the urine can be collected as a morning void/spot urine sample and/or as a mid-day void/spot urine sample. As shown in the Examples, membrane vesicles are present in urine collected at various timepoints during a day and can be isolated from both freshly collected and previously frozen urine samples. In some embodiments, the urine can also be clarified to remove, for example, casts, bacteria, and cell debris, prior to isolation of membrane vesicles by filtration. In some embodiments, the urine is clarified by low-speed centrifugation, such as for example at about 3,000×g, 2,000×g, 1,000×g, or less. The supernatant can then be collected, which contains the membrane vesicles, and further processed using the methods disclosed herein to isolate the exosomes.

The major components of diagnostic interest in urine are, in decreasing size order:
a) Urinary casts and bacteria
b) Membrane vesicles (e.g., exosomes)
c) Cryoglobulins
d) Soluble, high molecular weight proteins
e) Low molecular weight proteins and peptides
f) Electrolytes and low molecular weight metabolites.

Each of these component categories can have diagnostic value and can each be separated from the others and either processed immediately for analysis or for storage or later analysis. Thus, the presently disclosed subject matter encompasses the separation of membrane vesicles from biological fluids as well as other components from one another. Each of these components can then be analyzed individually by techniques generally known in the art to provide data useful in diagnosing or characterizing the progression of a disorder.

The structures purified from urine by the presently disclosed methods, as demonstrated in the Examples, have the correct distribution of diameters and morphology as provided within the scientific literature for urinary exosomes. The membrane vesicles' protein contents are demonstrated in the Examples by mass spectrometric and immunologic methods to be further consistent with literature documentation for exosomal proteins.

In some embodiments, the filtration module utilized to isolate the membrane vesicles from the biological sample is a fiber-based filtration cartridge. In some embodiments, the fibers are hollow polymeric fibers, such as for example polypropylene hollow fibers. In these embodiments, sample can be introduced into the filtration module by pumping the sample fluids into the module with a pump device, such as for example a peristaltic pump. The pump flow rate can vary, but in some embodiments, the pump flow rate is set at about 2 mL/minute.

In some embodiments, the filtration module utilized to isolate the membrane vesicles from the biological sample is a membrane filtration module. For example, in some embodiments, the membrane filtration module comprises a filter disc membrane (e.g., a hydrophilic polyvinylidene difluoride (PVDF) filter disc membrane) housed in a stirred cell apparatus (e.g., comprising a magnetic stirrer). In some embodiments, the sample moves through the filter as a result of a pressure gradient established on either side of the filter membrane.

In some embodiments, the filter within the filtration module that retains the membrane vesicles (i.e., the retentate) from the biological fluid sample (i.e., the filtrate) has an average pore diameter sufficient for exosome retention and permeation of all but the largest proteins. For example, in some embodiments, the filter has an average pore diameter of about 0.01 μm to about 0.15 μm, and in some embodiments from about 0.05 μm to about 0.12 μm. In some embodiments, the filter has an average pore diameter of about 0.06 μm, 0.07 μm, 0.08 μm, 0.09 μm, 0.1 μm, or 0.11 μm. In some embodiments, the filter utilized comprises a material having low hydrophobic absorptivity and/or high hydrophilic properties. In particular embodiments, the filter has an average pore size for exosome retention and permeation of most proteins as well as a surface that is hydrophilic, thereby limiting protein adsorption. Similar filters with these properties can also be suitably used with the presently disclosed subject matter. For example, in some embodiments, the filter comprises a material selected from the group consisting of polypropylene, PVDF, polyethylene, polyfluoroethylene, cellulose, secondary cellulose acetate, polyvinylalcohol, and ethylenevinyl alcohol (EVAL®, Kuraray Co., Okayama, Japan). Additional materials that can be utilized in filters of certain embodiments include, but are not limited to, polysulfone and polyethersulfone.

The retentate comprising the isolated membrane vesicles is collected from the filtration module. In some embodiments, the retentate is collected by flushing the retentate from the filter. Selection of a filter composition having hydrophilic surface properties, thereby limiting protein adsorption, can facilitate easier collection of the retentate and minimize use of harsh or time-consuming collection techniques. Once collected the membrane vesicles and/or associated polypeptide biomarkers can be further purified and/or concentrated and finally suspended in a suitable buffer solution, such as for example phosphate buffered saline (PBS), depending on how the vesicles and/or polypeptides will be utilized.

Once isolated, the membrane vesicles can be analyzed to identify characteristics of the vesicles, including identification and/or quantitation of exosomal polypeptides. Identification and/or quantitation of polypeptides within the vesicle can provide information related to biomarkers expressed within a subject. The identification of biomarkers expressed in a subject can be utilized to diagnose a disorder in a subject, monitor the progress of treatment of a disorder in a subject, and generally determine the state of health of a subject as a baseline, or as compared to a previously determined biomarker analysis.

As such, the presently disclosed subject matter provides methods of identifying and/or quantitating biomarker polypeptides from a biological fluid sample using the membrane vesicle isolation methods disclosed herein. The isolated membrane vesicles can then be subjected to polypeptide separation and/or analysis procedures generally known in the art to identify and quantitate the biomarker polypeptides associated with the isolated vesicles.

The presently disclosed subject matter further provides methods of diagnosing a disorder or measuring a disorder state in a subject utilizing the membrane vesicle isolation techniques disclosed herein in combination with polypeptide isolation and quantitation techniques. For example, water channel aquaporin 2 (AQP2) is a biomarker for certain water-balance disorders and identification of peptide variants expressed by a subject can provide information related to diagnosis of the disorders. Other non-limiting examples of disorders that can be diagnosed and/or monitored based on biomarker identification and/or quantitation include, but are not limited to diabetes, myocardial ischemia (troponin); cardiovascular risk (C-reactive protein, homocysteine); prostatic hypertrophy and prostatic cancer (PSA); systemic lupus erythematosus (ANA); and rheumatoid arthritis (Rheumatoid factor), with non-limiting exemplary biomarkers listed in parenthesis.

Further with respect to the diagnostic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

As disclosed, polypeptides from the isolated membrane vesicles can be separated and analyzed to identify and/or quantitate the polypeptides. Polypeptide separation techniques are generally known in the art and include, for example, electrophoretic and/or chromatographic techniques (e.g., liquid chromatography) and immunoisolation. Polypeptide identification and quantitation techniques are also well-known in the art.

Numerous methods and devices are well known to the skilled artisan for the detection and analysis of polypeptides, which are applicable to detection and analysis of isolated biomarker peptides associated with isolated exosomes. For example, mass spectrometry and/or immunoassay devices and methods can be used, although other methods are well-known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. These devices and methods can utilize labeled molecules in various sandwich, competitive, or non-competitive assay formats, to generate a signal that is related to the presence and/or amount of a biomarker polypeptide of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

In certain embodiments of the presently disclosed subject matter, the biomarker peptides are analyzed using an immunoassay. The presence or amount of a biomarker peptide can be determined using antibodies or fragments thereof specific for each marker and detecting specific binding. For example, in some embodiments, the antibody specifically binds a polypeptide of Table 1. In some embodiments, the antibody is a monoclonal antibody. Any suitable immunoassay can be utilized, for example, Western blots, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the markers is also contemplated by the present subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on solid support. This strip can then be dipped into the test biological sample and then processed quickly through washes and detection steps to generate a measurable signal, such as for example a colored spot.

The analysis of a plurality of markers is contemplated by the presently disclosed subject matter and can be carried out separately or simultaneously with one or more test samples. Several markers can be combined into one test for efficient processing of a multiple of samples. In addition, one skilled in the art would recognize the value of testing multiple samples (for example, at successive time points) from the same subject. Such testing of serial samples provides for the identification of changes in biomarker polypeptide levels over time. Increases or decreases in marker levels, as well as the absence of change in marker levels, can provide useful information about the disease status that includes, but is not limited to identifying the approximate time from onset of the event, the presence and amount of salvageable tissue, the appropriateness of drug therapies, the effectiveness of various therapies as indicated by reperfusion or resolution of symptoms, differentiation of the various types of a disorder, identification of the severity of the event, identification of the disease severity, and identification of the subject's outcome, including risk of future events.

A panel consisting of biomarkers associated with a disorder can be constructed to provide relevant information related to the diagnosis or prognosis of the disorder and management of subjects with the disorder. Such a panel can be constructed, for example, using 1, 2, 3, 4, 5, 6, 7, 8, 9, 10, 15 or 20 individual biomarkers. The analysis of a single marker or subsets of markers comprising a larger panel of markers could be carried out by one skilled in the art to optimize clinical sensitivity or specificity in various clinical settings. These include, but are not limited to ambulatory, urgent care, critical care, intensive care, monitoring unit, insubject, outsubject, physician office, medical clinic, and health screening settings. The analysis of biomarker polypeptides could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

In some embodiments, a kit for the isolation and analysis of biomarker polypeptides is provided that comprises a filtration module comprising a filter having an average pore diameter of between about 0.01 μm and about 0.15 μm and antibodies or fragments thereof having specificity for one or more biomarker polypeptides of interest. Such a kit can comprise devices and reagents for the analysis of at least one test sample. The kit can further comprise instructions for using the kit and conducting the analysis. Optionally the kit can contain one or more reagents or devices for converting a marker level to a diagnosis or prognosis of the subject.

Further, mass spectrometry is a useful and well-characterized tool for polypeptide identification and quantitation, alone or in combination with polypeptide separation techniques, particularly when coupled with bioinformatics analysis. Peptide molecular weights and the masses of sequencing ions can be obtained routinely using mass spectrometry to an accuracy which enables mass distinction amongst most of the 20 amino acids in the genetic code, as well as quantitation of peptides in a sample. Single or tandem mass spectrometry can be used. In tandem mass spectrometry, a peptide sample is introduced into the mass spectrometer and is subjected to analysis in two mass analyzers (denoted as MS1 and MS2). In MS1, a narrow mass-to-charge window (typically 2-4 Da), centered around the m/z ratio of the peptide to be analyzed, is selected. The ions within the selected mass window are then subjected to fragmentation via collision-induced dissociation, which typically occurs in a collision cell by applying a voltage to the cell and introducing a gas to promote fragmentation. The process produces smaller peptide fragments derived from the precursor ion (termed the 'product' or 'daughter' ions). The product ions, in addition to any remaining intact precursor ions, are then passed through to a second mass spectrometer (MS2) and detected to produce a fragmentation or tandem (MS/MS) spectrum. The MS/MS spectrum records the m/z values and the instrument-dependent detector response for all ions exiting from the collision cell. Fragmentation across the chemical bonds of the peptide backbone produces ions that are either charged on the C-terminal fragment (designated as x, y or z ions) or on the N-terminal fragment (a, b or c ions). Peptides are fragmented using two general approaches, high and low energy collision-induced dissociation (CID) conditions. In low energy CID experiments, signals assigned to y and b ions and from losses of water and ammonia are usually the most intense. During high energy CID, peptide molecules with sufficient internal energy to cause cleavages of the amino acid side chains are produced. These side chain losses predominantly occur at the amino acid residue where the backbone cleavage occurs. The general designations for these ions are d for N-terminal and w for C-terminal charged fragments, respectively. Other useful sequencing ions occur which result from a y-type cleavage at one residue and a b type cleavage at another residue along the polypeptide backbone (internal fragment ions) (Biemann, 1990; Papayannopoulos, 1995).

In one embodiment of the presently disclosed subject matter, the polypeptides are separated and analyzed using matrix-assisted laser-desorption time-of-flight mass spectrometry (MALDI-TOF). This instrument configuration is used to generate a primary mass spectrum in order to determine the molecular weight of the polypeptide. Other mass spectrometric techniques include, without limitation, time-of-flight, Fourier transform ion cyclotron resonance, quadrupole, ion trap, and magnetic sector mass spectrometry and compatible combinations thereof. See for example U.S. Pat. Nos. 6,925,389; 6,989,100; and 6,890,763 for further guidance, each of which is incorporated by reference herein in its entirety.

With regard to proteomic analysis, various computer-mediated methods are known for deducing the sequence of a peptide from an MS/MS spectrum. In one approach, 'subsequencing' strategies are used whereby portions of the total sequence, (i.e., sub-sequences) are tested against the mass spectrum (see Ishikawa et al., 1986; Siegel et al., 1988; Johnson et al., 1989, each of which is hereby incorporated by reference in its entirety). In this approach, sub-sequences that read or correlate to ions observed in the MS/MS spectrum are extended by a residue and the whole process is then repeated until the entire sequence is obtained. During each incremental extension of the sequence, the possibilities are reduced by comparing sub-sequences with the mass spectrum and only permitting continuation of the process for sub-sequences giving the most favorable spectral matches. Determination of amino acid composition has also been utilized to limit sequence possibilities (Zidarov et al., 1990, hereby incorporated by reference in its entirety).

Another approach utilizes computer programs for de novo peptide sequencing from fragmentation spectra based on graph theory (Fernandez-de-Cossio et al., 1995; Hines et al., 1995; Knapp, 1995, which are hereby incorporated by reference in their entirety). The basic method involves mathematically transforming an MS/MS spectrum into a form where fragment ions are converted to a single fragment ion type represented by a vertex on the spectrum graph (Bartels, 1990, the contents of which is hereby incorporated by reference in its entirety). Peptide sequences are then determined by finding the longest series of these transformed ions with mass differences corresponding to the mass of an amino acid.

Other methods match spectral information with sequences in protein and translated nucleotide sequence databases. An algorithm has been described for searching protein and nucleotide databases with mass and sequence information from fragmentation spectra of tryptic peptides (MS-TAG) (Mann and Wilm, 1994; Clauser et al., 1996, which are hereby incorporated by reference in their entirety). A comparison with the fragmentation spectra of the same peptide after methylation of the carboxyl groups or enzymatic digestion in the presence of 180 water to incorporate 180 into the C-terminal carboxy groups (Shevchenko et al., 1997, which is hereby incorporated by reference in its entirety) can provide even more accurate results. A similar approach has been extended to the analysis of intact proteins using laser fragmentation and Fourier-transform mass spectrometry (Mortz, E. et al., 1996, which is hereby incorporated by reference in its entirety).

Another approach has been described for identifying peptide sequences from database interrogation by comparing the experimental fragmentation spectrum with theoretical spectra from a mass-constrained set of database sequences (SEQUEST) (U.S. Pat. No. 5,538,897; Yates et al., 1991, which are hereby incorporated by reference in their entirety). For each candidate sequence within the database spectrum, a theoretical fragmentation spectrum is formed according to a selected ion model of peptide fragmentation. The predicted theoretically derived mass spectra are compared to each of the experimentally derived fragmentation spectra by a cross-correlation function for scoring spectra.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Materials and Methods for Examples

Urine collection. A 50-200 mL waste specimen void was collected using a) sample containers prealiquoted with protease inhibitors (PEFABLOC® SC (Pentapharm Ltd., Basel, Switzerland) 0.1 mg/mL and aprotinin 0.01 mg/mL) and bacteriastat (sodium azide; 0.5 mM final concentration) and/or b) immediately centrifuged at 3000×g to sediment particulate matter (e.g. cells and casts). The clarified urine was decanted and the samples not intended for use in exosome sampling were stored at −80° C. until analysis.

Exosome sampling. To avoid differential loss of exosomes during cryoprecipitate formation and collection, the freshly centrifuged, protease inhibited supernatant is filtered through a dead-end hollow fiber module containing polypropylene hollow fibers with an average pore diameter of 0.1 µm. (Membrana Gmbh., Wuppertal, Germany). The urine is introduced into the exosome-filtration module using a peristaltic pump operating at a 2 mL/min flow rate. The dead volume of the entire module is less than 1.5 ml, so that the exosome proteins (the retentate) can be harvested by introducing that volume of a) PBS—for exosome recovery or b) IEF equilibration buffer, fortified with trifluoroethanol for direct dissolution of exosomal proteins.

Alternatively, the clarified urine is filtered through a Millipore (Bedford, Mass., U.S.A.) 45 mm diameter, 0.1 µm pore size type VVLP filtration disc housed in an AMICON® (Millipore) 50 mL stirred cell apparatus with 60 psi $N_2$ and magnetic stirrer. Filtered material is rinsed with 50 mL phosphate buffered saline (PBS), pH 7.4. The retained rinse volume (2-3 mL) is saved and the filter is sonicated in 4 mL PBS for 10 min. The filter rinse volumes are combined and then divided between to ultracentrifuge tubes. Exosomes are pelleted as described below. Alternatively, proteins from the four (4) mL sample containing the exosomes can be isolated using precipitation (such as with trichloroacetic acid/acetone) or the exosomes can be concentrated by spin ultrafiltration (Millipore Ultra 4 spin filters) using a bench-top centrifuge (at 4,000×g). To evaluate the effects of storage, urine is collected and immediately frozen at −80° C. Urine is maintained for 2-6 months before thawing and processing as described above.

Figure 2:
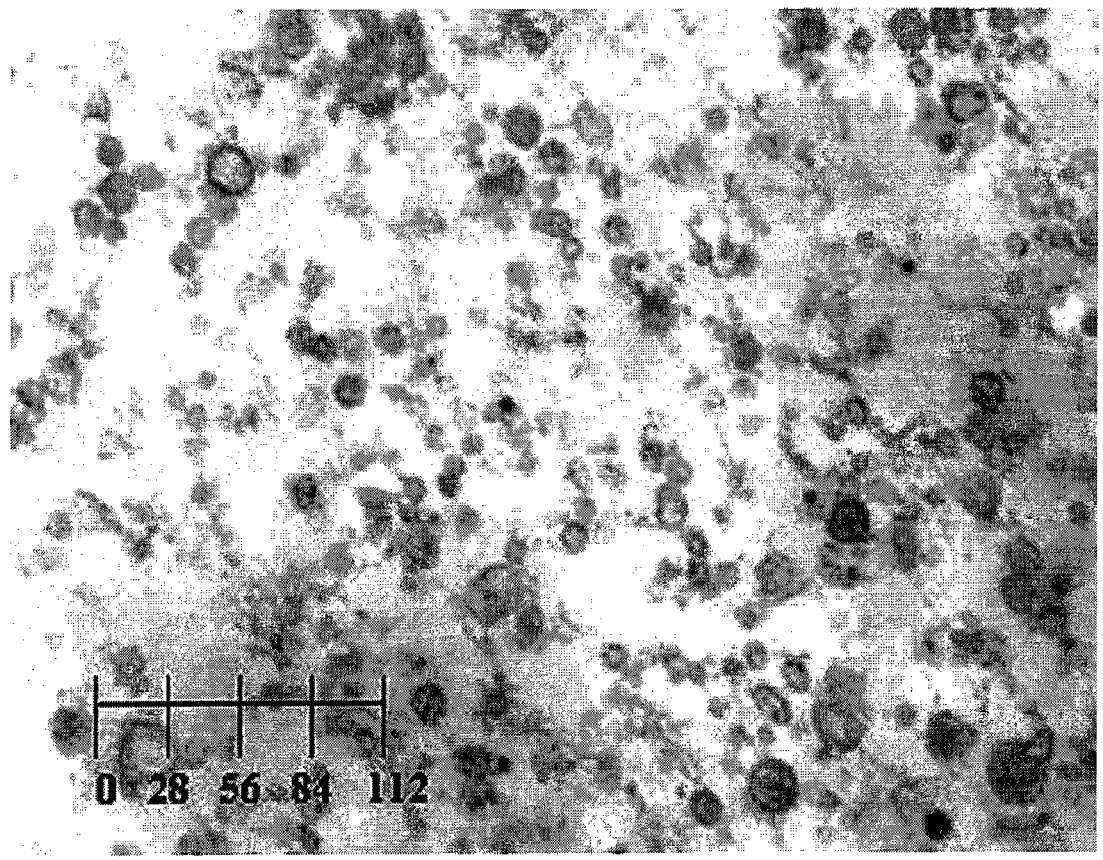
FIG. 2 is a transmission electron micrograph (TEM) of filtered urinary exosomes from fresh urine. Urine is collected by the clean catch method and 1× protease inhibitors added. Urine was spun at 3,000×g to remove debris/casts/bacteria and subsequently filtered using a membrane fiber-based filtration cartridge as disclosed herein. Filtered vesicles are washed with 10 mL PBS and then collected (back-flushed) from the cartridge with 3.5 mL PBS. The PBS back-flush is spun at 200,000×g to pellet low density vesicular bodies. The low-density vesicular pellet is cross-linked in a 4% glutaraldehyde/PBS solution and analyzed by TEM. The fiduciary mark is in units of nm. Imaged spheroids have diameters consistent with known exosomal diameters (30-80 nm).
Figure 3:
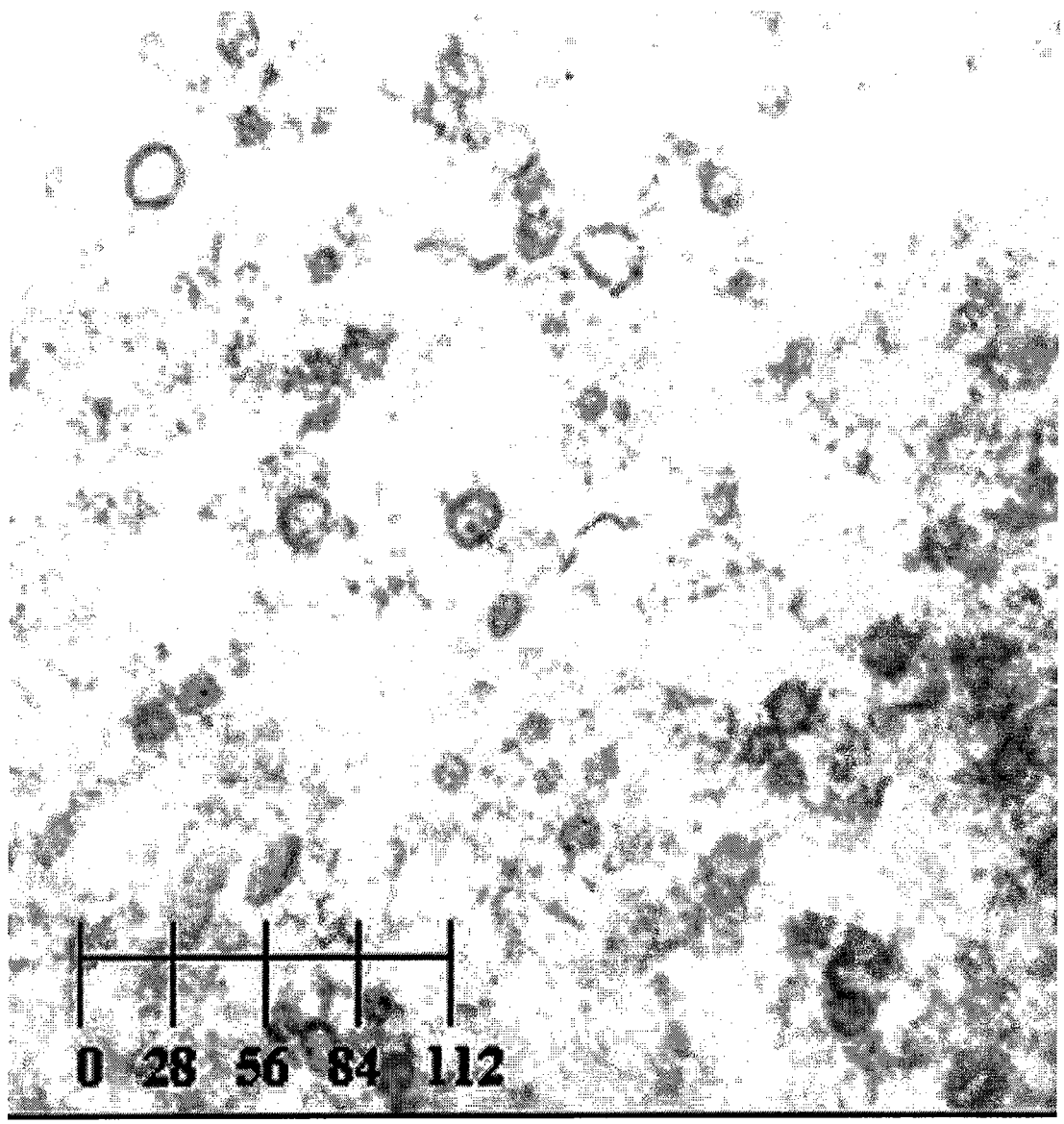
FIG. 3 is a transmission electron micrograph (TEM) of filtered urinary exosomes from frozen urine. Urine is collected by the clean catch method, 1× protease inhibitors added, and frozen for >8 months at −80° C. The urine is thawed at room temperature, spun at 3,000×g to remove cryoglobulin/debris/casts/bacteria and subsequently filtered using a disc filter membrane as disclosed herein. Filtered vesicles are washed with 10 mL PBS and then collected (by rinsing) from the filtration disc with 3.5 mL PBS. The PBS rinse is spun at 200,000×g to pellet low density vesicular bodies. The low-density vesicular pellet is cross-linked in a 4% glutaraldehyde/PBS solution and analyzed by TEM. Fiduciary mark is in units of nm. Imaged spheroids have diameters consistent with known exosomal diameters (30-80 nm).

Exosome samples recovered in PBS were used for TEM characterization. PBS containing exosomes were pelleted by high speed ultracentrifugation at 200,000×g. PBS was removed by pipetting and 4% glutaraldehyde in PBS was layered onto the exosomal pellet. Exosomal-protein glutaraldehyde-crosslinking was allowed to proceed for 1 h. The cross linked pellet was submitted for TEM analysis. (FIGS. 2 & 3)

Post-Exosome Sample Handling. Samples previously frozen at −80° C. were thawed at room temperature. Cryoprecipitate formed upon thawing is pelleted by centrifugation (3000×g; 15 min). Urine was concentrated with AMICON® stirred cell concentrators (Millipore) using 10,000 MWCO YM-type (regenerated cellulose) membrane filters and $N_2$ gas for positive pressure. Urine samples were routinely concentrated from the original starting volume down to 1-2 mL final volume. The concentrated urine samples (retentates) were transferred into 0.5-3.0 mL, 10,000 Dalton MWCO SLIDE-A-LYZER® (Pierce Biotechnology, Inc., Rockford, Ill., U.S.A.) for standardization of pH and ionic strength. Samples were dialyzed overnight at 4° C. against 4L 2-5 mM Tris pH 7.4. The urine filtrate containing low molecular weight species such as peptides, intermediary metabolites from carbohydrate and protein degradation, and also salts is labeled and frozen at −80° C. for future studies.

The urinary protein, following removal of cellular debris, exosomes, cryoglobulins, and peptides now can be concentrated by conventional methods in order to allow high molecular weight protein a) electrophoretic separation or b) trypsinization followed by direct peptide separation using capillary HPLC. Protein concentration values for the standardized urine protein samples were determined by either a Biorad (Bradford) protein microassay or Pierce (pBCA) protein microassay against a bovine serum albumin (BSA) standard.

One-dimensional, denaturing, reducing electrophoresis and Western blotting. Exosomal protein and urinary protein is reduced and denatured by heating to 90° C. for 5 min in the presence of 1×LDS gel loading buffer (Invitrogen, California, U.S.A.) supplemented with dithiothreitol 20 mM (DTT). Protein is loaded into 4-12% NUPAGE® gels (Invitrogen, Carlsbad, Calif., U.S.A.) and electrophoresis at 200V until the bromophenol blue running dye migrated to the end of the gel.

Protein samples were quantified using a Pierce pBCA protein assay. Protein samples (5-20 µg) were resolved on 4-12% SDS-NUPAGE® gels (Invitrogen) using Mark12 molecular weight standards and HK2 cell lysates or total urine protein as positive controls when possible. Proteins were electroblotted onto 0.45 µm nitrocellulose membranes for 60 min at 20V. Electroblotted gels were stained with colloidal Coomassie blue stain to evaluate transfer. Blotted membranes were blocked in 5% milk proteins dissolved in a 1× Tris-Tween 20 (TTBS) solution for 2 h at room temperature or overnight at 4° C. Primary antibody (0.2 µg/mL-1.0 µg/mL) was dissolved in 5% albumin in TTBS and incubated on the blocked membrane for 1 h at room temperature or overnight at 4° C. Secondary antibody (0.05 µg/mL-0.2 µg/mL) was dissolved in 5% albumin in TTBS and incubated on the blocked membrane for 2 h at room temperature or overnight at 4° C. The blotted membrane was rinsed 5-times for 5 min between all steps. Secondary antibody conjugated with horseradish peroxidase (HRP) was visualized using the Pierce Femto-Super Signal Kit. Membranes were used to expose x-ray film and resulting images were developed and scanned and bands quantified.

Protein digestion, peptide mass finger printing and sequence tagging. The stained gel slabs were washed with 18MΩ water and each spot was punched with a clean pipette tip trimmed to produce a 1-3 mm³ punch. Gel pieces were conditioned at room temperature for 15 min with 20 µL 0.1M ammonium bicarbonate ($NH_4HCO_3$) followed with direct addition of 30 µL acetonitrile (99.9%). The solution was removed after 15 min and the gel pieces were dried using a Jouan Model RC 10.10 speed vacuum centrifuge. The gel pieces were rehydrated with 20 µL of 0.02M dithiothreitol in 0.1M $NH_4HCO_3$ and incubated at 56° C. for 45 min to reduce the protein. The sample was cooled to room temperature and the solution was removed and replaced by 0.055M iodoacetamide in 0.1M $NH_4HCO_3$. The alkylation of the gel plugs proceeded for 30 min in the dark whereupon the solution was replaced by 200 µL 0.05M $NH_4HCO_3$ and incubated for 15 min. The gel plugs were dehydrated by the addition of 200 µL 99.9% acetonitrile. After 15 min, the solution was removed and the gel plugs were dried by vacuum centrifuge and re-hydrated with 5 µL of 20 ng/µL modified trypsin (Promega, Madison, Wis., U.S.A.) in 0.05M $NH_4HCO_3$. Re-hydrated gel pieces were covered with 5 µL 0.05M $NH_4HCO_3$ solution and incubated overnight at 37° C. The digested samples were cooled and the trypsinization reaction was stopped by the addition of 1 µL 0.1% TFA.

MALDI matrix used throughout analysis was α-cyano-4-hydroxycinnamic acid (α-CN) containing 10 mM $NH_4H_2PO_4$. Samples were a) spotted as 1:1 (v/v) samples of protein digest: α-CN (or b) desalted sample aliquots (0.7 µL-1.0 µL, 4 mg/mL α-CN, 50% acetonitrile 0.1% TFA) spotted directly onto MALDI sample targets using C18 Zip Tips. Samples were air-dried in the dark and were cleared of particulate matter with compressed gas prior to sample plate loading into the mass spectrometer.

Positive ion MALDI-TOF mass spectra were acquired using an Applied Biosystems (Foster City, Calif.) AB4700 protein analyzer operating in reflectron mode and with ion source pressure ~0.5 µTorr. After a 400 ns time-delayed ion extraction period, the ions were accelerated to 20 kV for time-of-flight (TOF) mass spectrometric analysis. A total of 600 to 1000 laser shots (355 nm Nd:YAG solid state laser operating at 200 Hz) were acquired and signal averaged. Data was analyzed using Mascot (version 1.9) assuming a) monoisotopic peptides masses, b) cysteine carbamidomethylation, b) variable oxidation of methionine, c) maximum of one missed trypsin cleavage, and d) a mass accuracy of greater than 150 ppm. Limitation of the original protein mass was not employed within the Mascot search.

Example 1

Urine Collection and Exosome Characterization

Spherical membrane vesicles (e.g., exosomes) were purified from fresh and from previously-frozen urine using two independent filtration methods-1) tangential filtration with fiber-based filtration cartridges and 2) membrane filtration with disc-membranes, as disclosed herein. See FIG. 1. Exosomes were recovered from a) thawed, previously frozen urine despite formation of cryoprecipitate and b) urine collected as morning or day-time voids. Exosome collection methods allowed for desalting and rinsing of residual urine volume from the exosomes. Recovered exosomes were characterized for physical morphology using transmission electron microscopy (TEM) (FIGS. 2 and 3) and for protein composition using 1-dimensional, denaturing-reducing polyacrylamide electrophoresis (1D SDS PAGE) and subsequent protein identification by mass spectrometry and bioinformatic analysis (Pisitkun et al., 2004; Caby et al., 2005; Gatti et al., 2005). Protein identification was achieved by mass spectrometric methods (peptide sequence tagging) and by antibody based methods (Western blotting).

Example 2

One-Dimensional Electrophoresis and Western Blotting

Exosomal proteins were denatured, reduced, and resolved by mass using a 4-12% NUPAGE® gel (Invitrogen). Separated proteins were electro-blotted onto nitrocellulose membranes and proteins detected with antibodies specific to proteins previously identified to be present in urinary exosomes (ezrin, neprilysin, and the α-subunit of the $Na^+/K^+$ ATPase).

Figure 4:
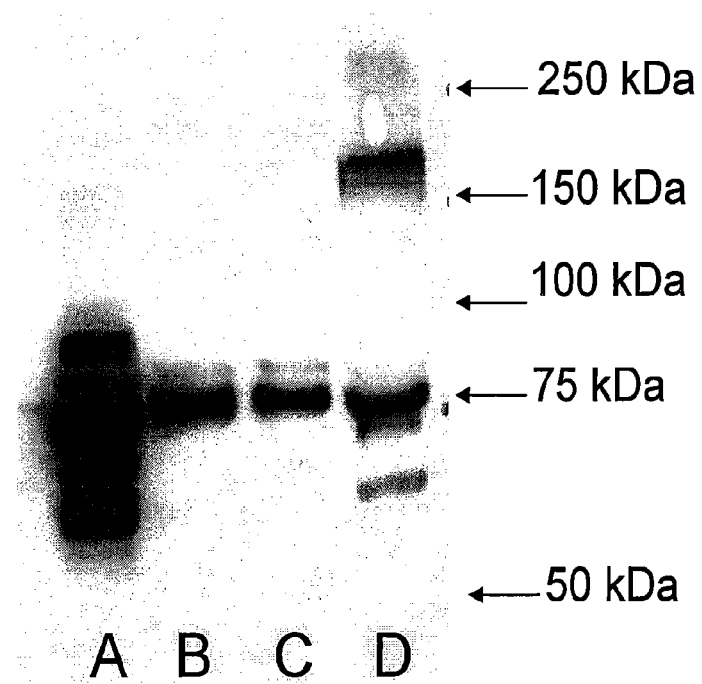
FIG. 4 is an immunoblot image showing the peripheral membrane protein ezrin co-purifies with urinary exosomes. Exosomal pellets were re-solubilized with 1×LDS Laemmli buffer and separated on a 4-12% gradient gel. Proteins were transferred to nitrocellulose (0.45 µm) by tank transfer (25V, 1 h) and blotted in 5% non-fat milk TTBS. Primary rabbit anti ezrin (human) Ig was incubated with the blot at 4° C. overnight. Following three 5 min TTBS rinses, secondary goat anti-rabbit Ig-HRP conjugate was incubated with the blot at room temperature for 2 h. Following three 5 min TTBS rinses, the blot was reacted with SUPERSIGNAL WEST PICO® chemiluminescent substrate (Pierce Biotechnology, Inc., Rockford, Ill., U.S.A.) for 1 min and exposed to film. Ezrin MW=80 kDa (Lane A, positive control-HEK plasma membrane; Lane B, morning void; Lane C, mid-day void 1; Lane D, mid-day void 2).

Ezrin is a peripheral membrane protein that physically interacts with integral membrane proteins such as CD43 or CD44 at the cytoplasmic face of the plasma membrane. The data demonstrate that ezrin co-purifies with urinary exosomes filtered from morning and also from mid-day void urine samples (FIG. 4). The identification of ezrin co-purification is consistent with established literature (Pisitkun et al., 2004; Gatti et al., 2005; Hegmans et al., 2004).

Figure 5:
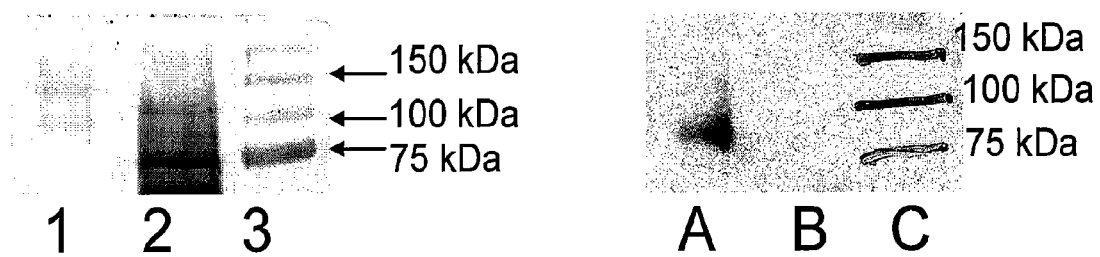
FIG. 5 is a series of immunoblot images showing the integral membrane protein Na+/K+ ATPase, α-subunit copurifies with urinary exosomes. An exosomal pellet isolated by fiber filtration from fresh normal male urine was re-solubilized with 1×LDS Laemmli buffer and separated on a 4-12% gradient gel. Proteins were transferred to nitrocellulose (0.45 µm) by tank transfer (25V, 1 h) and blotted in 5% non-fat milk TTBS. After blotting, the gel was stained with Coomassie brilliant blue overnight and imaged using a LI-COR Odyssey Infrared Imaging Station. (Lane 1, residual exosomal pellet protein; Lane 2 Residual Filter fiber rinse protein; Lane 3, residual molecular weight standards). Primary mouse anti Na+/K+ ATPase α-subunit (human) Ig was incubated with the blot at 4° C. overnight. Following three 5 min TTBS rinses, secondary rabbit anti-mouse Ig-HRP conjugate was incubated with the blot at room temperature for 2 h. Following three 5 min TTBS rinses, the blot was reacted with SUPERSIGNAL WEST PICO® chemiluminescent substrate (Pierce Biotechnology, Inc.) for 1 min and exposed to film. Na+/K+ ATPase α-subunit MW=90 kDa (Transferred Gel: Lane 1, Exosomal pellet; Lane 2, Filter fiber rinse; Lane 3, Molecular Weight Standards; Western Blot: Lane A Exosomal pellet; Lane B, Filter fiber rinse; Lane C, Molecular Weight Standards).

The α-subunit of the $Na^+/K^+$ ATPase catalyzes the hydrolysis of ATP, coupled with the exchange of sodium and potassium ions across the plasma membrane. The proteins are located in the cell membrane and are members of the P-type cation-transporting ATPase superfamily, and as such have 10 transmembrane (TM) helices. It was demonstrated by Western blotting that the α-subunit of the Na+/K+ ATPase co-purifies with urinary exosomes using tangential fiber filtration (FIG. 5). Furthermore, the data demonstrate that the exosome recovery is complete as the protein is absent in the filter fiber stripping solution [Laemmli buffer supplemented with an organic co-solvent (40% trifluoroethanol; TFE)] designed to maximize the recovery of hydrophobic proteins and peptides. Identification of the α-subunit of the Na+/K+ ATPase is consistent with the scientific literature (Mellegol et al., 2005; van Niel et al., 2001).

Figure 6:
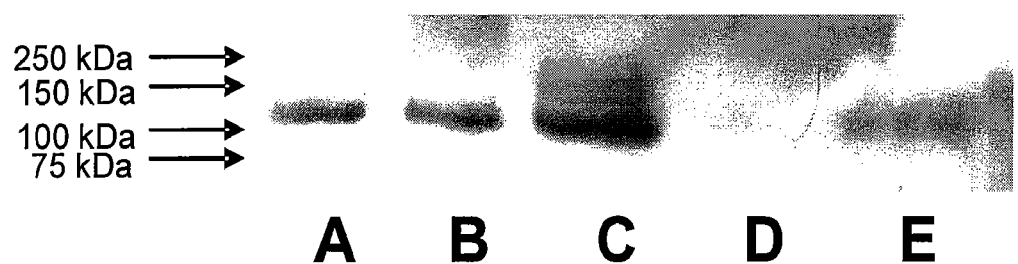
FIG. 6 is an immunoblot image showing the integral membrane protein neprilysin (CD10) co-purifies with urinary exosomes. An exosomal pellet isolated by disc filtration from fresh normal male urine was re-solubilized with 1×LDS Laemmli buffer and separated on a 4-12% gradient gel. Proteins were transferred to nitrocellulose (0.45 µm) by tank transfer (25V, 1 h) and blotted in 5% non-fat milk TTBS. Primary mouse anti CN 10 (human) Ig was incubated with the blot at 4° C. overnight. Following three 5 min TTBS rinses, secondary rabbit anti-mouse Ig-HRP conjugate was incubated with the blot at room temperature for 2 h. Following three 5 min TTBS rinses, the blot was reacted with SUPERSIGNAL WEST PICO® chemiluminescent substrate (Pierce Biotechnology, Inc.) for 1 min and exposed to film. Na+/K+ ATPase α-subunit MW=90 kDa (Lane A, Exosomal proteins following sucrose density spin; Lane B, Exosomal proteins following DTT reduction with subsequent sucrose density spin; Lane C, Exosomal pellet; Lane D, Filtered-urine urinary proteins; Lane E, Unfiltered-urine urinary proteins).
Figure 7:
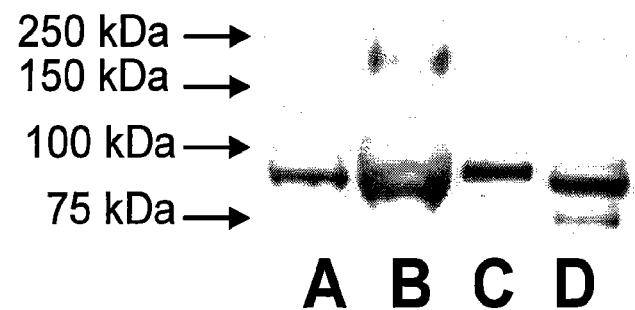
FIG. 7 is an immunoblot image showing neprilysin (CD10) co-purifies with urinary exosomes isolated using either an exosomal filtration cartridge or a filtration disc and from either fresh or frozen urine. An exosomal pellet isolated using cartridge filtration or using disc filtration from fresh normal male urine or previously frozen normal male urine was re-solubilized with 1×LDS Laemmli buffer and separated on a 4-12% gradient gel. Proteins were transferred to nitrocellulose (0.45 µm) by tank transfer (25V, 1 h) and blotted in 5% non-fat milk TTBS. Primary mouse anti CN10 (human) Ig was incubated with the blot at 4° C. overnight. Following three 5 min TTBS rinses, secondary rabbit anti-mouse Ig-HRP conjugate was incubated with the blot at room temperature for 2 h. Following three 5 min TTBS rinses, the blot was reacted with SUPERSIGNAL WEST PICO® chemiluminescent substrate (Pierce Biotechnology, Inc.) for 1 min and exposed to film. Na+/K+ ATPase α-subunit MW=90 kDa (Lane A, fresh urine & disc filtration; Lane B, frozen urine & disc filtration; Lane C, fresh urine & fiber filtration; Lane D, frozen urine & fiber filtration).

Neprilysin is a Type II membrane protein and has a single transmembrane helix. Neprilysin is a major constituent of the renal brush border membrane. It was demonstrated by Western blotting that neprilysin co-purifies with exosomes using both fiber and membrane filtration methods and including both fresh and frozen urine. Additionally, using neprilysin immunoblots, it was demonstrated that the exosome filtration method depletes the urine of the neprilysin co-purifying material (exosomes) (FIGS. 6 and 7). The co-purification of neprilysin is consistent with the scientific literature (Pisitkun et al., 2004; Gatti et al., 2005).

The most abundant urinary protein (the Tamm-Horsfall protein; THP) is heavily glycosylated and is predisposed to the formation of aggregates. These aggregates have molecular weight distribution from ~90 kDa up to >1,000 kDa. Published procedures for removal of THP aggregates include chemical denaturation via hot DTT and differential sucrose-density ultracentrifugation. By Western blotting it was demonstrated that either method can be used as a sample pre-treatment without significant loss of neprilysin.

Example 3

Protein Digestion, Peptide Mass Fingerprinting and Sequence Tagging

Figure 8:
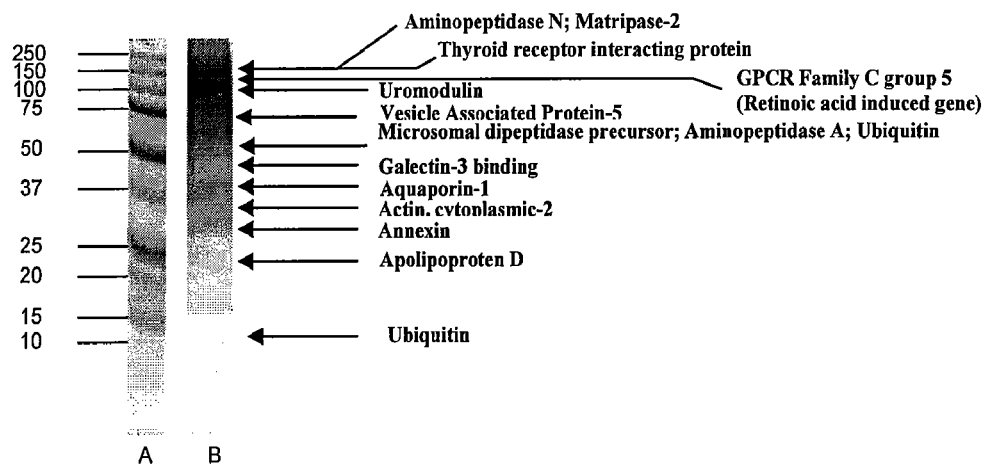
FIG. 8 is a 1D-SDS PAGE gel image showing expected urinary exosomal proteins are identified by MALDI-MS following 1D SDS-PAGE separation. Isolated exosome filtrate is re-solubilized with 1×LDS Laemmli buffer and separated on a 4-12% gradient gel. The sample lane is divided into 2.5 mm cubes, conditioned, reduced, alkylated, and digested with trypsin. Trypsin digests are analyzed by MALDI-TOF MS and MALDI-TOF MS-MS. Representative proteins identified are annotated on the gel image; the annotations are positioned to illustrate the gel slice origin of the identified protein.

Isolated exosomes were dissolved into Laemmli buffer and separated on a 4-12% gradient gel (FIG. 8). The length of the sample lane was cut into 2.5 mm² cubes, protein content reduced and alkylated, and digested with trypsin. The trypsin digest were analyzed by MALDI-TOF MS with selective fragmentation of dominant precursor ions. Peptide sequence tagging supported by peptide mass fingerprint analysis was used to identify proteins co-purifying with urinary exosomes.

Included in the list of identified proteins are a) transmembrane (TM) proteins, b) ubiquinated proteins, c) ligands of advance glycosylation end product (AGE) modified proteins and d) membrane associated proteolytic enzymes. The identified proteins include several proteins with documented relevance to human diseases were identified within the analyzed samples.

Example 4

Direct Analysis, One Dimensional Reversed-Phase Liquid Chromatography and Electrospray Ionization Mass Spectrometry Isolated exosomes were dispersed into a solution adjusted to contain a buffering solution of 0.1 M triethylammonium bicarbonate, pH 8.5 and a detergent solution of 0.1% NP-40. Proteins co-isolated with the exosomes were reduced by addition of 2 mm tris-carboxyethylphosphine/0.1 M triethylammonium bicarbonate, pH 8.5 with heating to 5° C. for 30 min. Protein samples were then cooled and reduced by 1 h incubation in the dark with addition of 20 mM iodoacetamide/0.1 M triethylammonium bicarbonate, pH 8.5. Proteins were then digested by addition of 250 ng mass spectrometry grade, modified trypsin, and incubation at 37° C. for 1 hr with shaking. After 1 h a second aliquot (250 ng) of mass spectrometry grade trypsin was added and incubation continued overnight for a total digestion time of 20 h.

The trypsin digest was separated by one-dimensional reversed-phase liquid chromatography and eluting peptide ions mass quantified, fragmented and fragments mass analyzed by linear ion trap mass spectrometry. The fragmentation spectra were analyzed using SEQUEST SORCERER™ (Sage N Research, San Jose, Calif., U.S.A.) and PEPTIDE PROPHET & PROTEIN PROPHET™ (Institute of Systems Biology, Seattle, Wash., U.S.A.) to filter the SEQUEST data. Identified proteins included membrane proteins identified in EXAMPLE 2 and annotated on FIG. 8. (See also Table 1.)

Discussion of Examples 1-4

As illustrated by the Examples herein, the present methods were successfully utilized to isolate exosomes from biological samples and identify proteins associated with the isolated exosomes. The present methods thus allow for isolation and enrichment of particular protein populations of interest that can provide information as to biological processes within a subject, such as for example the presence or absence of disease and responses to therapeutic treatments. For example,

TABLE 1

TABLE 1. Membrane proteins identified by direct analysis of trypsin digested exosomes using one-dimensional reversed phase liquid chromatography and electrospray ionization linear ion trap mass spectrometry with peptide fragmentation analysis using SEQUEST SORCERER ™ and PEPTIDE PROPHET & PROTEIN PROPHET ™ to filter the SEQUEST data. Proteins identified are indicative of exosome isolation.

| No. | Accession No. | % Sequence Coverage | No. Unique Peptides | Total No. Peptides | Protein Name and Description |
|---|---|---|---|---|---|
| 1 | 31377806 | 11.6 | 8 | 17 | Polymeric immunoglobulin receptor [*Homo sapiens*] |
| 2 | 4502095 | 12.1 | 10 | 12 | Membrane alanine aminopeptidase M [*Homo sapiens*] |
| 3 | 6042200 | 12.3 | 7 | 8 | Membrane metallo-endopeptidase; neprilysin [*Homo sapiens*] |
| 4 | 40217833 | 19.9 | 6 | 7 | GPCR Family C-5-C-b; retinoic acid responsive gene protein [*Homo sapiens*] |
| 5 | 28916691 | 12.1 | 4 | 5 | Mucin 1; episialin [*Homo sapiens*] |
| 6 | 4506153 | 7.6 | 2 | 4 | Prostasin preproprotein [*Homo sapiens*] |
| 7 | 4557849 | 3.8 | 3 | 3 | Sodium potassium chloride cotransporter 2 [*Homo sapiens*] |
| 8 | 7706451 | 3 | 1 | 1 | GPCR Family C-5-B precursor; retinoic acid responsive gene protein [*Homo sapiens*] |
| 9 | 11386147 | 2.9 | 1 | 1 | Prosaposin [*Homo sapiens*] |
| 10 | 21264578 | 5.4 | 1 | 1 | Tetraspan 1; TM4SF [*Homo sapiens*] |
| 11 | 4557503 | 3.3 | 10 | 15 | Cubilin [*Homo sapiens*] |
| 12 | 6806919 | 2.7 | 9 | 12 | Megalin [*Homo sapiens*] |
| 13 | 5174387 | 4 | 2 | 3 | Prominin 1 [*Homo sapiens*] |
| 14 | 17511435 | 3.7 | 2 | 2 | Roundabout homolog 4 [*Homo sapiens*] |
| 15 | 18765694 | 3.1 | 2 | 2 | Dipeptidylpeptidase IV (CD26) [*Homo sapiens*] |
| 16 | 19923603 | 3.5 | 1 | 2 | Cytochrome b reductase 1 [*Homo sapiens*] |
| 17 | 24497519 | 4.1 | 2 | 2 | Mannosidase, alpha, class 1A, member 1 [*Homo sapiens*] |
| 18 | 32313593 | 6.9 | 2 | 2 | Olfactomedin 4 precursor [*Homo sapiens*] |
| 19 | 4502179 | 7.7 | 1 | 1 | Aquaporin 2 [*Homo sapiens*] |
| 20 | 4758190 | 2.4 | 1 | 1 | Dipeptidase 1 (renal) [*Homo sapiens*] |
| 21 | 4759140 | 3.9 | 1 | 1 | Solute carrier family 9 (sodium\hydrogen exchanger), isoform 3 regulator 1 [*Homo sapiens*] |
| 22 | 13376868 | 2 | 1 | 1 | NG22 protein; choline transporter-like protein 4 [*Homo sapiens*] |
| 23 | 14150145 | 2.9 | 1 | 1 | Limitrin [*Homo sapiens*] |
| 24 | 19923362 | 9.3 | 1 | 1 | Thy-1 T-cell antigen [*Homo sapiens*] |
| 25 | 33598950 | 3.8 | 1 | 1 | Podocalyxin-like precursor [*Homo sapiens*] | exosome protein compositions have been demonstrated to include transmembrane proteins such as CD10, the alpha subunit of the Na+/K+ ATPase and peripheral membrane protein such as ezrin by immunochemical methods. Further demonstration of selective enrichment for low abundant urine proteins can be achieved using the presently disclosed exosome isolation methods.

Tables 2 and 3 provide exemplary data of proteins isolated and identified from either exosome isolates using the presently disclosed methods or from human urine samples, respectively. Proteins listed in both tables were identified using computer aided data analysis (PEPTIDE PROPHET & PROTEIN PROPHET™) of exosome protein tryptic digests developed using 1D-LC-MS/MS sample analysis. A comparison between Tables 2 and 3 of the proteins identified and quantities of the proteins demonstrate selective enrichment for proteins of interest associated with urinary exosomes. Four such proteins are discussed hereinbelow as non-limiting examples demonstrating the selective enrichment of exosomal proteins from urine. Two transmembrane proteins (megalin and cubulin) are selected to demonstrate enrichment of exosomal proteins from urine. Two serum proteins (albumin and kininogen-1) are selected to demonstrate selective filtering of proteins from the exosomal protein preparation.

Megalin and cubulin are two proteins resident in the apical membrane of the renal proximal tubule. The functions of these proteins are well documented. These proteins are known to function as protein scavengers and are responsible for recycling of urinary albumin from urine. Further, presence of these proteins in urinary exosomes is well documented. As demonstrated in Table 2, megalin represents 4.84 percent of the total share of all MS/MS spectral identifications from the LC-MS/MS analysis of tryptic exosome protein fragments. Additionally, cubulin represents 2.96 percent of the total share of all MS/MS spectral identifications from the LC-MS/MS analysis of tryptic exosome protein fragments. In contrast, and as demonstrated in Table 3, megalin represents only 0.47 percent of the total share of all MS/MS spectral identifications from the LC-MS/MS analysis of tryptic urine protein fragments. Additionally, cubulin represents only 0.4 percent of the total share of all MS/MS spectral identifications from the LC-MS/MS analysis of tryptic urine protein fragments. Thus, use of the presently disclosed novel methods resulted in a several-fold enrichment of these two integral-membrane proteins.

Albumin and kininogen-1 are well documented plasma proteins and are known to be in the urine at low levels in normal conditions. Renal damage resulting from trauma or from genetic factors can present with increased levels of these two plasma proteins in the urine. As demonstrated in Table 2, albumin represents 4.88 percent of the total share of all MS/MS spectral identifications from the LC-MS/MS analysis of tryptic exosome protein fragments. Additionally, cubulin represents 0.66 percent of the total share of all MS/MS spectral identifications from the LC-MS/MS analysis of tryptic exosome protein fragments. In contrast, and as demonstrated in Table 3, albumin represents 32.05 percent of the total share of all MS/MS spectral identifications from the LC-MS/MS analysis of tryptic urine protein fragments. Additionally, kininogen-1 represents 3.03 percent of the total share of all MS/MS spectral identifications from the LC-MS/MS analysis of tryptic urine protein fragments. Albumin and kininogen-1 are not selectively depleted from the urine. Thus, use of the presently disclosed novel microfiltration methods provided for depletion of otherwise very abundant plasma proteins found in the urine. The small presence of the two proteins in the exosome protein preparation is presumed to be from normal biology and the renal-urine protein recycling mechanisms.

TABLE 2

| ID# | Protein gi Number | Protein Probability Score | Percent Coverage | Number of Unique Peptides | Total Number of Peptides | % Share of Spectrum ID's | Protein ID |
| --- | --- | --- | --- | --- | --- | --- | --- |
| 1 | 21735625 | 0.82 | 4.9 | 1 | 1 | 0.09 | 14-3-3 zeta |
| 2 | 13489091 | 1 | 9.1 | 2 | 2 | 0.22 | 3-Mercaptopyruvate sulfurtransferase |
| 3 | 6912586 | 0.95 | 6.2 | 1 | 1 | 0.1 | 6-Phosphogluconolactonase |
| 4 | 4502211 | 0.44 | 6.3 | 1 | 1 | 0.05 | ADP-ribosylation factor 6 |
| 5 | 21493031 | 0.82 | 0.9 | 1 | 2 | 0.39 | A-kinase anchor protein 13 isoform 3; guanine nucleotide exchange factor Lbc |
| 6 | 4502027 | 1 | 38.3 | 27 | 47 | 4.88 | Albumin |
| 7 | 21361176 | 0.98 | 2.6 | 1 | 1 | 0.11 | Aldehyde dehydrogenase 1A1 |
| 8 | 51466516 | 0.42 | 2.5 | 1 | 1 | 0.1 | Aldo-keto reductase family 1, member B10 |
| 9 | 40354205 | 0.99 | 3.6 | 1 | 1 | 0.11 | Aldolase B |
| 10 | 4501881 | 1 | 15.7 | 3 | 4 | 0.36 | Alpha 1 actin precursor |
| 11 | 4504347 | 1.00 | 10.6 | 1 | 2 | 0.36 | Alpha 1 globin |
| 12 | 18641350 | 0.99 | 0.9 | 1 | 1 | 0.11 | Alpha 1 type XV collagen precursor |
| 13 | 21071030 | 1 | 8.7 | 4 | 4 | 0.43 | Alpha 1B-glycoprotein |
| 14 | 17986277 | 0.99 | 1.5 | 2 | 4 | 0.26 | Alpha 2 type IV collagen preproprotein; canstatin |
| 15 | 4501843 | 0.99 | 2.5 | 1 | 1 | 0.11 | Alpha-1-antichymotrypsin |
| 16 | 4502067 | 1 | 21.9 | 6 | 14 | 1.54 | Alpha-1-microglobulin\bikunin |
| 17 | 4502005 | 1 | 10.4 | 4 | 11 | 0.79 | Alpha-2HS-glycoprotein |
| 18 | 4505327 | 1 | 13.2 | 6 | 6 | 0.59 | Alpha-N-acetylglucosaminidase |
| 19 | 4502085 | 1 | 12.3 | 5 | 5 | 0.55 | Amylase, pancreatic, alpha-2A |
| 20 | 6912236 | 0.99 | 6.7 | 3 | 3 | 0.19 | Angiopoietin-related protein 2 |
| 21 | 4502107 | 1.00 | 13.4 | 3 | 3 | 0.57 | Annexin 5 |
| 22 | 4557317 | 1 | 10.7 | 3 | 3 | 0.34 | Annexin A11 |
| 23 | 4757756 | 1.00 | 7.7 | 2 | 2 | 0.38 | Annexin A2 isoform 2 |
| 24 | 4502105 | 0.99 | 5 | 1 | 1 | 0.11 | Annexin IV |
| 25 | 51476111 | 1 | 14.6 | 3 | 3 | 0.32 | Apolipoprotein A-I precursor (Apo-AI) |
| 26 | 4502151 | 0.54 | 4.5 | 2 | 2 | 0.16 | Apolipoprotein A-IV precursor |
| 27 | 4502163 | 1 | 30.7 | 5 | 14 | 1.09 | Apolipoprotein D precursor |
| 28 | 4557325 | 1 | 17.7 | 4 | 4 | 0.43 | Apolipoprotein E3 |
| 29 | 4502179 | 0.99 | 7.7 | 1 | 1 | 0.21 | Aquaporin 2 |
| 30 | 4557337 | 0.87 | 3.2 | 1 | 1 | 0.1 | Argininosuccinate synthetase |

TABLE 2-continued

| ID# | Protein gi Number | Protein Probability Score | Percent Coverage | Number of Unique Peptides | Total Number of Peptides | % Share of Spectrum ID's | Protein ID |
|---|---|---|---|---|---|---|---|
| 31 | 15149476 | 0.83 | 1.7 | 1 | 1 | 0.09 | Arginyl-tRNA synthetase |
| 32 | 4504067 | 0.83 | 1.9 | 1 | 1 | 0.09 | Aspartate aminotransferase 1 |
| 33 | 42741659 | 0.96 | 1.5 | 1 | 1 | 0.2 | ATP-binding cassette sub-family B member 1 |
| 34 | 21450861 | 0.99 | 1.1 | 1 | 1 | 0.11 | Attractin isoform 1; mahogany protein |
| 35 | 21536466 | 0.99 | 2.6 | 2 | 2 | 0.14 | AXL receptor tyrosine kinase isoform 1 |
| 36 | 4504349 | 1 | 25.9 | 2 | 2 | 0.24 | Beta globin |
| 37 | 4502407 | 0.99 | 3.9 | 1 | 1 | 0.19 | Betaine-homocysteine methyltransferase 1 |
| 38 | 13162290 | 0.97 | 2.8 | 1 | 1 | 0.24 | Betaine-homocysteine methyltransferase 2 |
| 39 | 7706083 | 0.71 | 1.6 | 1 | 1 | 0.17 | C1r-like serine protease analog |
| 40 | 8923765 | 0.41 | 1.2 | 1 | 1 | 0.08 | Calcium channel alpha2-delta3 subunit |
| 41 | 4557395 | 1 | 14.6 | 2 | 2 | 0.15 | Carbonic anhydrase B |
| 42 | 51464068 | 0.95 | 2.7 | 1 | 1 | 0.1 | Carboxypeptidase N 83 kDa chain |
| 43 | 4503143 | 0.53 | 1.9 | 1 | 4 | 0.21 | Cathepsin D preproprotein |
| 44 | 4557417 | 1 | 16.8 | 7 | 9 | 0.99 | CD14 antigen precursor |
| 45 | 21361193 | 1 | 3 | 3 | 3 | 0.32 | CD44 antigen |
| 46 | 42761474 | 1 | 25 | 5 | 18 | 1.95 | CD59 |
| 47 | 4757952 | 1.00 | 19.9 | 3 | 4 | 0.55 | Cell division cycle 42 isoform 1 |
| 48 | 4557485 | 1 | 3.8 | 3 | 4 | 0.6 | Ceruloplasmin |
| 49 | 31542306 | 0.62 | 7 | 1 | 1 | 0.14 | CHMP1.5 protein; C18orf2 |
| 50 | 4557443 | 0.99 | 3 | 1 | 1 | 0.11 | Cholesteryl ester transfer protein, plasma precursor |
| 51 | 40255141 | 0.53 | 3 | 1 | 4 | 0.13 | Chondroitin beta1,4 N-acetylgalactosaminyltransferase |
| 52 | 21361741 | 0.98 | 2.9 | 1 | 1 | 0.24 | Chromosome 6 open reading frame 55; My012 protein |
| 53 | 42716297 | 1 | 23.8 | 10 | 16 | 1.68 | Clusterin isoform 1 |
| 54 | 8922699 | 0.97 | 3.4 | 1 | 1 | 0.11 | CNDP dipeptidase 2 |
| 55 | 4503635 | 0.82 | 1.4 | 1 | 1 | 0.09 | Coagulation factor II precursor |
| 56 | 15011913 | 1 | 6.5 | 4 | 4 | 0.27 | Collagen, type VI, alpha 1 precursor |
| 57 | 10834974 | 1 | 2.7 | 2 | 2 | 0.2 | Complement component (3b\4b) receptor-1 isoform F precursor |
| 58 | 4557379 | 1 | 11.6 | 5 | 6 | 0.62 | Complement component 1 inhibitor precursor |
| 59 | 4557385 | 1 | 2 | 2 | 2 | 0.47 | Complement component 3 precursor; acylation-stimulating protein cleavage product |
| 60 | 4503015 | 0.41 | 1.7 | 1 | 1 | 0.1 | Copine III |
| 61 | 21536286 | 1 | 7.9 | 2 | 2 | 0.22 | Creatine kinase-B |
| 62 | 4503057 | 0.41 | 4.6 | 1 | 1 | 0.08 | Crystallin, alpha B |
| 63 | 4557503 | 1 | 8.6 | 26 | 30 | 2.96 | Cubilin |
| 64 | 19923603 | 0.62 | 3.5 | 1 | 1 | 0.07 | Cytochrome b reductase 1 |
| 65 | 4503355 | 0.45 | 0.7 | 1 | 1 | 0.05 | Dedicator of cyto-kinesis 1 |
| 66 | 4758190 | 1 | 14.4 | 4 | 8 | 1.57 | Dipeptidase 1 (renal) |
| 67 | 18765694 | 1.00 | 3.1 | 2 | 2 | 0.38 | Dipeptidylpeptidase IV (CD26, adenosine deaminase complexing protein 2) |
| 68 | 40254866 | 0.46 | 4.7 | 1 | 1 | 0.09 | DKFZP564O123 protein |
| 69 | 4503281 | 0.97 | 2.1 | 1 | 1 | 0.24 | Dopa decarboxylase (aromatic L-amino acid decarboxylase) |
| 70 | 9665262 | 0.95 | 1.9 | 1 | 1 | 0.11 | EGF-containing fibulin-like extracellular matrix protein 1 isoform a precursor; fibrillin-like |
| 71 | 46195707 | 1 | 1.1 | 2 | 2 | 0.22 | EGF-like-domain, multiple 4 |
| 72 | 21264315 | 0.99 | 5.5 | 1 | 1 | 0.23 | EH-domain containing 4 |
| 73 | 4503571 | 1 | 9 | 3 | 3 | 0.73 | Enolase 1 |
| 74 | 4503491 | 1 | 16.4 | 26 | 50 | 5.04 | Epidermal growth factor |
| 75 | 21264616 | 0.76 | 1.7 | 1 | 1 | 0.19 | Epidermal growth factor receptor pathway substrate 8-like protein 2 |
| 76 | 7657058 | 0.65 | 2.6 | 1 | 1 | 0.12 | Eukaryotic translation initiation factor 2B, subunit 2 beta, 39 kDa |
| 77 | 21614499 | 1 | 17.1 | 7 | 8 | 0.5 | Ezrin |
| 78 | 45238580 | 0.47 | 3.6 | 1 | 1 | 0.09 | F-box only protein 13 |
| 79 | 4503681 | 0.83 | 1.9 | 1 | 1 | 0.13 | Fc fragment of IgG binding protein |
| 80 | 47132549 | 1 | 1.9 | 3 | 3 | 0.32 | Fibronectin 1 isoform 6 preproprotein |
| 81 | 16579888 | 0.99 | 4.7 | 1 | 1 | 0.11 | Fructose-1,6-bisphosphatase 1 |
| 82 | 40217833 | 1 | 13.2 | 6 | 9 | 0.97 | G protein-coupled receptor family C, group 5, member C isoform b |
| 83 | 7706451 | 1 | 6 | 2 | 2 | 0.22 | G protein-coupled receptor, family C, group 5, member B precursor |
| 84 | 10834966 | 1 | 7.8 | 4 | 4 | 0.43 | Galactosidase, beta 1 |
| 85 | 5031863 | 1 | 18.1 | 16 | 39 | 4.13 | Galectin 3 binding protein |
| 86 | 4501887 | 1 | 18.9 | 5 | 9 | 0.84 | Gamma 1 actin |
| 87 | 4885271 | 1.00 | 8.3 | 3 | 3 | 0.47 | Gamma-glutamyl transpeptidase |
| 88 | 6598323 | 0.98 | 6.1 | 1 | 1 | 0.21 | GDP dissociation inhibitor 2 |
| 89 | 38044288 | 0.76 | 1.1 | 1 | 2 | 0.24 | Gelsolin isoform b |
| 90 | 6912618 | 0.51 | 4.2 | 1 | 1 | 0.06 | Glutaminyl-peptide cyclotransferase precursor |
| 91 | 7669492 | 1 | 12.8 | 3 | 4 | 0.43 | Glyceraldehyde-3-phosphate dehydrogenase |
| 92 | 40254926 | 0.98 | 22.2 | 1 | 1 | 0.11 | G-protein gamma-12 subunit |
| 93 | 4557617 | 0.85 | 1.3 | 1 | 1 | 0.09 | Growth arrest-specific 6; AXL stimulatory factor |

TABLE 2-continued

| ID# | Protein gi Number | Protein Probability Score | Percent Coverage | Number of Unique Peptides | Total Number of Peptides | % Share of Spectrum ID's | Protein ID |
|---|---|---|---|---|---|---|---|
| 94 | 4504037 | 0.99 | 4.2 | 1 | 1 | 0.19 | Guanine nucleotide binding protein, alpha 11 (Gq class) |
| 95 | 11321585 | 1 | 5 | 2 | 6 | 0.56 | Guanine nucleotide-binding protein G(I)\G(S)\G(T) beta subunit 1; beta subunit, signal-transducing proteins GS\GI, |
| 96 | 20357529 | 0.97 | 3.5 | 1 | 1 | 0.19 | Guanine nucleotide-binding protein G(I)\G(S)\G(T) beta subunit 2 |
| 97 | 34419635 | 0.50 | 4.5 | 1 | 1 | 0.14 | Heat shock 70 kD protein 6 (HSP70B') |
| 98 | 27436929 | 0.50 | 6.2 | 1 | 1 | 0.2 | Heat shock 70 kDa protein 1-like |
| 99 | 13676857 | 1.00 | 10.1 | 3 | 3 | 0.46 | Heat shock 70 kDa protein 2 |
| 100 | 51461017 | 0.52 | 5.2 | 1 | 1 | 0.13 | Heat shock cognate 71 kDa protein |
| 101 | 47607492 | 0.86 | 0.5 | 1 | 1 | 0.16 | Hemidesmosomal protein 1 |
| 102 | 7427517 | 1 | 0.3 | 1 | 1 | 0.24 | Heparan sulfate proteoglycan 2 (endorepellin; perlecan) |
| 103 | 51471096 | 0.74 | 2 | 1 | 1 | 0.08 | Heterogeneous nuclear ribonucleoprotein A1 |
| 104 | 16418389 | 0.99 | 5.7 | 1 | 1 | 0.11 | HGFL protein |
| 105 | 24308440 | 0.99 | 5.5 | 1 | 1 | 0.11 | Hypothetical protein BC011840 |
| 106 | 39930521 | 1 | 11.9 | 9 | 16 | 1.76 | Hypothetical protein BC013767 |
| 107 | 51466566 | 0.4 | 0.8 | 1 | 1 | 0.04 | Hypothetical protein CBG17606 [Poly Cystic Kidney Disease like protein 3] |
| 108 | 8923271 | 0.60 | 2.8 | 1 | 1 | 0.12 | Hypothetical protein FLJ20291 |
| 109 | 39752639 | 0.51 | 5.5 | 2 | 2 | 0.12 | Hypothetical protein FLJ22374 |
| 110 | 33342276 | 0.41 | 1.4 | 1 | 1 | 0.08 | Hypothetical protein FLJ22761 |
| 111 | 21389601 | 0.99 | 3.9 | 1 | 1 | 0.19 | Hypothetical protein FLJ32421 |
| 112 | 51466862 | 0.72 | 3.1 | 1 | 1 | 0.08 | Hypothetical protein XP_374254 |
| 113 | 51472926 | 0.98 | 8.9 | 1 | 2 | 0.22 | Ig heavy chain V-III region VH26 precursor |
| 114 | 51475407 | 1 | 14 | 2 | 2 | 0.22 | Ig kappa chain |
| 115 | 21489959 | 1 | 32.7 | 5 | 10 | 0.9 | Immunoglobulin J chain |
| 116 | 41150478 | 1 | 14.4 | 2 | 2 | 0.21 | Immunoglobulin M chain |
| 117 | 18874099 | 0.48 | 0.8 | 1 | 1 | 0.05 | Importin 4 |
| 118 | 4826772 | 1 | 5 | 2 | 2 | 0.21 | Insulin-like growth factor binding protein, acid labile subunit |
| 119 | 31542984 | 1 | 6.6 | 6 | 9 | 0.96 | Inter-alpha (globulin) inhibitor H4 (plasma Kallikrein-sensitive glycoprotein) |
| 120 | 4504875 | 0.99 | 5 | 1 | 1 | 0.11 | Kallikrein 1 preproprotein |
| 121 | 34222393 | 0.91 | 1.3 | 1 | 1 | 0.18 | Kinase suppressor of Ras-2 |
| 122 | 4504893 | 1 | 12.4 | 5 | 6 | 0.66 | Kininogen 1; alpha-2-thiol proteinase inhibitor; bradykinin |
| 123 | 4557032 | 1 | 14.7 | 4 | 5 | 0.46 | Lactate dehydrogenase B |
| 124 | 5803023 | 0.44 | 2.5 | 1 | 1 | 0.11 | Lectin, mannose-binding 2 |
| 125 | 16418467 | 1 | 12.7 | 4 | 6 | 0.5 | Leucine-rich alpha-2-glycoprotein 1 |
| 126 | 33636750 | 0.43 | 0.7 | 1 | 1 | 0.08 | Likely ortholog of mouse ubiquitin-conjugating enzyme E2-230K |
| 127 | 14150145 | 1 | 11.8 | 5 | 5 | 0.36 | Limitrin |
| 128 | 4503849 | 1 | 9.5 | 7 | 7 | 0.65 | Lysosomal alpha-glucosidase; acid maltase |
| 129 | 4504957 | 1 | 4.9 | 2 | 2 | 0.2 | Lysosome-associated membrane protein-2 |
| 130 | 38569482 | 0.78 | 1.3 | 1 | 1 | 0.09 | Maba1 |
| 131 | 4758712 | 1 | 1.1 | 2 | 2 | 0.22 | Maltase-glucoamylase |
| 132 | 21264363 | 0.99 | 8.6 | 1 | 1 | 0.11 | Mannan-binding lectin serine protease 2 isoform 1 precursor |
| 133 | 24497519 | 1 | 8.6 | 4 | 7 | 0.37 | Mannosidase, alpha, class 1A, member 1 |
| 134 | 5803088 | 0.60 | 0.7 | 1 | 1 | 0.12 | MAPK\ERK kinase kinase 4 |
| 135 | 6806919 | 1 | 6.1 | 27 | 40 | 3.84 | Megalin |
| 136 | 4502095 | 1 | 11.5 | 11 | 15 | 1.61 | Membrane alanine aminopeptidase M |
| 137 | 6042200 | 1 | 14.5 | 9 | 10 | 1.03 | Membrane metallo-endopeptidase; neprilysin |
| 138 | 5174551 | 0.42 | 2.1 | 1 | 2 | 0.08 | Meprin A, beta |
| 139 | 14249562 | 0.58 | 1.5 | 1 | 1 | 0.06 | Microtubule associated serine\threonine kinase-like |
| 140 | 46852147 | 0.72 | 1.3 | 1 | 1 | 0.14 | Mitochondrial isoleucine tRNA synthetase |
| 141 | 4505257 | 0.98 | 9.2 | 1 | 1 | 0.33 | Moesin |
| 142 | 28916691 | 1 | 12.5 | 4 | 6 | 0.59 | Mucin 1, transmembrane; episialin |
| 143 | 5174569 | 0.52 | 0.2 | 1 | 1 | 0.1 | Myeloid\lymphoid or mixed-lineage leukemia (trithorax (Drosophila) homolog) |
| 144 | 46430642 | 1 | 2.9 | 2 | 2 | 0.21 | Myosin IC |
| 145 | 4758754 | 1.00 | 3.8 | 2 | 2 | 0.36 | NAPSA gene product |
| 146 | 13376868 | 0.99 | 2 | 1 | 1 | 0.11 | NG22 protein; choline transporter-like protein 4 |
| 147 | 4505395 | 0.91 | 0.8 | 1 | 2 | 0.11 | Nidogen (entactin) |
| 148 | 5031985 | 0.54 | 11.8 | 1 | 1 | 0.06 | Nuclear transport factor 2 |
| 149 | 32313593 | 1 | 9.2 | 4 | 4 | 0.82 | Olfactomedin 4 precursor |
| 150 | 21361845 | 0.92 | 2.1 | 1 | 1 | 0.1 | Peptidoglycan recognition protein L precursor |
| 151 | 33188452 | 0.68 | 7.5 | 1 | 1 | 0.17 | Peroxiredoxin 2 isoform b |
| 152 | 4505621 | 1 | 16.6 | 3 | 3 | 0.23 | Phosphatidylethanolamine binding protein |
| 153 | 4505763 | 0.99 | 4.1 | 1 | 1 | 0.11 | Phosphoglycerate kinase 1 |
| 154 | 4505881 | 0.53 | 2 | 1 | 1 | 0.06 | Plasminogen |
| 155 | 33598950 | 1 | 3.8 | 2 | 2 | 0.21 | Podocalyxin-like precursor |
| 156 | 31377806 | 1 | 19.5 | 14 | 33 | 3.46 | Polymeric immunoglobulin receptor |

TABLE 2-continued

| ID# | Protein gi Number | Protein Probability Score | Percent Coverage | Number of Unique Peptides | Total Number of Peptides | % Share of Spectrum ID's | Protein ID |
|---|---|---|---|---|---|---|---|
| 157 | 4505959 | 0.57 | 1.9 | 1 | 1 | 0.06 | POU domain, class 2, transcription factor 2 |
| 158 | 4826898 | 0.75 | 11.4 | 1 | 1 | 0.08 | Profilin-1 |
| 159 | 7019485 | 0.99 | 6.8 | 1 | 1 | 0.11 | Programmed cell death 6; apoptosis-linked gene 2 |
| 160 | 22027538 | 1.00 | 7.6 | 6 | 8 | 1.18 | Programmed cell death 6-interacting protein |
| 161 | 5174387 | 1 | 8.6 | 5 | 6 | 0.57 | Prominin 1 |
| 162 | 21389623 | 1 | 3.4 | 2 | 2 | 0.21 | Prominin 2 |
| 163 | 11386147 | 1 | 4.2 | 1 | 1 | 0.12 | Prosaposin (sphingolipid activator protein-1) |
| 164 | 32171249 | 1 | 17.4 | 3 | 3 | 0.33 | Prostaglandin-H2 D-isomerase |
| 165 | 4506153 | 1 | 7.6 | 3 | 4 | 0.44 | Prostasin preproprotein |
| 166 | 6382064 | 1 | 21.2 | 6 | 6 | 0.65 | Prostatic acid phosphatase precursor |
| 167 | 4506013 | 0.76 | 5 | 1 | 1 | 0.15 | Protein phosphatase 1, regulatory subunit 7 |
| 168 | 4506121 | 1 | 9.8 | 3 | 4 | 0.44 | Protein Z, vitamin K-dependent plasma glycoprotein |
| 169 | 7656922 | 0.44 | 4.1 | 1 | 1 | 0.05 | Putative breast adenocarcinoma marker |
| 170 | 38372933 | 0.69 | 7.2 | 1 | 1 | 0.2 | Putative breast adenocarcinoma marker |
| 171 | 41281489 | 1 | 6.9 | 3 | 7 | 0.52 | Putative MAPK activating protein PM28 |
| 172 | 24431973 | 0.61 | 1.7 | 1 | 1 | 0.12 | Putative NFkB activating protein |
| 173 | 14165278 | 0.99 | 10.3 | 1 | 3 | 0.23 | Putative nuclear protein ORF1-FL49 |
| 174 | 33286418 | 1 | 4 | 2 | 2 | 0.21 | Pyruvate kinase 3 isoform 1; thyroid hormone-binding protein, cytosolic |
| 175 | 10835049 | 0.69 | 5.7 | 1 | 1 | 0.13 | Ras homolog gene family, member A; oncogene RHO H12; Aplysia ras-related homolog 12 |
| 176 | 34147513 | 0.99 | 6.8 | 1 | 1 | 0.11 | Ras-associated protein RAB7 |
| 177 | 7661678 | 1 | 12 | 2 | 2 | 0.16 | RAS-related protein RAP1B; K-REV |
| 178 | 4506403 | 0.98 | 3.6 | 1 | 1 | 0.19 | Retinoic acid induced 3 |
| 179 | 51474268 | 0.44 | 0.8 | 1 | 2 | 0.05 | RIKEN cDNA 3000004C01 |
| 180 | 17511435 | 1 | 3.7 | 2 | 2 | 0.24 | Roundabout homolog 4 |
| 181 | 5032057 | 0.99 | 15.2 | 1 | 1 | 0.11 | S100 calcium binding protein A11 (calgizzarin) |
| 182 | 9951915 | 0.99 | 3 | 1 | 1 | 0.19 | S-adenosylhomocysteine hydrolase |
| 183 | 4759166 | 1 | 18 | 4 | 8 | 0.88 | Secreted phosphoprotein 1 (osteopontin) |
| 184 | 21361198 | 1 | 6.2 | 3 | 3 | 0.27 | Serine (or cysteine) proteinase inhibitor, clade A, member 1 |
| 185 | 21361195 | 1 | 28.1 | 13 | 26 | 2.51 | Serine (or cysteine) proteinase inhibitor, clade A, member 5 |
| 186 | 4502133 | 0.99 | 5.8 | 1 | 2 | 0.22 | Serum amyloid P component precursor; pentaxin-related; 9.5S alpha-1-glycoprotein |
| 187 | 28827795 | 0.98 | 4.9 | 1 | 2 | 0.36 | Snf7 homologue associated with Alix 1 |
| 188 | 4557849 | 1.00 | 3.8 | 3 | 3 | 0.58 | Sodium potassium chloride cotransporter 2; Na—K-2Cl cotransporter |
| 189 | 4507013 | 0.99 | 2.2 | 1 | 1 | 0.24 | Solute carrier family 2 (facilitated glucose\fructose transporter), member 5 |
| 190 | 4759140 | 0.97 | 3.9 | 1 | 1 | 0.11 | Solute carrier family 9 (sodium\hydrogen exchanger), isoform 3 regulator 1 |
| 191 | 18201911 | 1 | 8.4 | 3 | 3 | 0.33 | Somatomedin B; epibolin |
| 192 | 4507155 | 0.59 | 2.5 | 1 | 2 | 0.26 | Sorbitol dehydrogenase |
| 193 | 38016907 | 0.53 | 9.8 | 1 | 1 | 0.13 | Stomatin isoform b |
| 194 | 29029530 | 0.47 | 4.1 | 1 | 1 | 0.09 | Sulfotransferase 1C1 |
| 195 | 4507151 | 1 | 5.4 | 2 | 2 | 0.22 | Superoxide dismutase 3, extracellular |
| 196 | 33239443 | 0.88 | 4.6 | 1 | 1 | 0.1 | Synaptophysin-like protein isoform b |
| 197 | 29568086 | 0.98 | 5.5 | 1 | 1 | 0.11 | Syndecan 1 |
| 198 | 5032083 | 1.00 | 6.4 | 1 | 1 | 0.19 | Syndecan binding protein (syntenin) |
| 199 | 21264578 | 0.99 | 5.4 | 1 | 2 | 0.22 | Tetraspan 1 |
| 200 | 4507745 | 0.97 | 12.4 | 1 | 1 | 0.19 | Thioredoxin |
| 201 | 40317626 | 0.64 | 1 | 1 | 1 | 0.07 | Thrombospondin 1 precursor |
| 202 | 19923362 | 0.99 | 9.3 | 1 | 2 | 0.19 | Thy-1 T-cell antigen |
| 203 | 33356179 | 0.66 | 1.5 | 1 | 1 | 0.13 | Transcription termination factor, RNA polymerase I |
| 204 | 4557871 | 1 | 14.8 | 8 | 10 | 0.84 | Transferrin |
| 205 | 41058276 | 1 | 9.2 | 2 | 2 | 0.22 | Triosephosphate isomerase 1 |
| 206 | 51470965 | 0.4 | 1.3 | 1 | 1 | 0.04 | Tripartite motif-containing 48 |
| 207 | 5729770 | 0.99 | 3.2 | 1 | 1 | 0.11 | Tripeptidyl-peptidase I precursor |
| 208 | 13376539 | 0.99 | 5.8 | 1 | 1 | 0.11 | Tubulin, alpha 4 |
| 209 | 51473011 | 1 | 44.7 | 3 | 4 | 0.95 | Ubiquitin C |
| 210 | 4507833 | 1 | 23.3 | 32 | 254 | 23.19 | Uromodulin; Tamm-Horsfall glycoprotein |
| 211 | 5803215 | 1.00 | 8.7 | 1 | 1 | 0.19 | Uroplakin 2 |
| 212 | 17865802 | 1 | 6.8 | 2 | 2 | 0.2 | Vacuolar protein sorting factor 4B; suppressor of K+ transport defect 1 |
| 213 | 41327712 | 0.75 | 8.3 | 1 | 1 | 0.14 | V-crk sarcoma virus CT10 oncogene homolog isoform a |
| 214 | 4507879 | 1 | 7.8 | 2 | 2 | 0.49 | Voltage-dependent anion channel 1 |
| 215 | 15451943 | 0.68 | 1.6 | 1 | 1 | 0.13 | Zinc finger protein 6 |

TABLE 3

| ID# | Protein gi Number | Protein Probability Score | Percent Coverage | Number of Unique Peptides | Total Number of Peptides | % Share of Spectrum ID's | Protein ID |
|---|---|---|---|---|---|---|---|
| 1 | 4503849 | 1 | 8 | 5 | 7 | 0.61 | Acid alpha-glucosidase preproprotein |
| 2 | 4501987 | 0.55 | 2 | 2 | 3 | 0.07 | Afamin precursor; alpha-albumin |
| 3 | 41151826 | 0.41 | 0.6 | 1 | 1 | 0.04 | Agrin |
| 4 | 4502027 | 1 | 54.4 | 65 | 412 | 32.05 | Albumin precursor |
| 5 | 4501881 | 0.99 | 4.3 | 1 | 1 | 0.11 | Alpha 1 actin |
| 6 | 18641350 | 1 | 2.2 | 3 | 3 | 0.24 | Alpha 1 type XV collagen precursor |
| 7 | 21071030 | 0.99 | 2.4 | 1 | 2 | 0.19 | Alpha 1B-glycoprotein |
| 8 | 4501843 | 1 | 8.8 | 3 | 5 | 0.41 | Alpha-1-antichymotrypsin |
| 9 | 4502067 | 1 | 23.9 | 9 | 28 | 2.78 | Alpha-1-microglobulin\bikunin precursor |
| 10 | 4502337 | 1 | 32.6 | 10 | 18 | 1.47 | Alpha-2-glycoprotein, zinc |
| 11 | 4502005 | 1 | 12 | 6 | 12 | 1.01 | Alpha-2HS-glycoprotein |
| 12 | 4505327 | 1 | 7 | 4 | 4 | 0.42 | Alpha-N-acetylglucosaminidase |
| 13 | 40254482 | 1 | 33.9 | 2 | 2 | 0.86 | Amylase, alpha 1A |
| 14 | 4502085 | 1 | 33.3 | 3 | 5 | 1.08 | Amylase, pancreatic, alpha-2A |
| 15 | 10280622 | 1 | 34.4 | 3 | 3 | 0.95 | Amylase, pancreatic, alpha-2B |
| 16 | 28376664 | 0.96 | 2.3 | 2 | 2 | 0.16 | AN1, ubiquitin-like, homolog |
| 17 | 6912236 | 1 | 2.3 | 1 | 1 | 0.11 | Angiopoietin-like 2 precursor |
| 18 | 4502151 | 0.77 | 2.8 | 1 | 1 | 0.08 | Apolipoprotein A-IV precursor |
| 19 | 4502163 | 1 | 32.8 | 6 | 22 | 1.85 | Apolipoprotein D precursor |
| 20 | 4557325 | 0.72 | 2.8 | 1 | 1 | 0.07 | Apolipoprotein E precursor |
| 21 | 4557337 | 1 | 6.3 | 2 | 2 | 0.21 | Argininosuccinate synthetase |
| 22 | 15149476 | 0.61 | 1.7 | 1 | 1 | 0.06 | Arginyl-tRNA synthetase |
| 23 | 6005990 | 0.99 | 2.8 | 1 | 1 | 0.11 | Arylsulfatase A precursor |
| 24 | 27262647 | 0.53 | 2.3 | 1 | 2 | 0.06 | Ataxin 2 related protein isoform A |
| 25 | 10947135 | 0.83 | 1.4 | 1 | 4 | 0.21 | ATP-binding cassette, sub-family F, member 1; ATP-binding cassette 50; ATP-binding cassette 50 (TNF-alpha stimulated) |
| 26 | 21536466 | 0.98 | 1.2 | 1 | 2 | 0.18 | AXL receptor tyrosine kinase isoform 1 |
| 27 | 4557327 | 1 | 4.9 | 2 | 2 | 0.2 | Beta-2-glycoprotein I precursor |
| 28 | 4757826 | 1 | 16.8 | 3 | 3 | 0.3 | Beta-2-microglobulin precursor |
| 29 | 6453813 | 0.98 | 3.3 | 1 | 1 | 0.1 | Butyrophilin, subfamily 2, member A2 isoform a |
| 30 | 4757960 | 1 | 5.3 | 4 | 4 | 0.31 | Cadherin 1, type 1 preproprotein (epithelial) |
| 31 | 16306532 | 0.96 | 1.7 | 1 | 1 | 0.1 | Cadherin 11, type 2 isoform 1 preproprotein |
| 32 | 4502719 | 0.99 | 3.8 | 1 | 2 | 0.15 | Cadherin 13 preproprotein |
| 33 | 38327526 | 0.97 | 2.3 | 1 | 1 | 0.1 | Carboxypeptidase M precursor |
| 34 | 51464068 | 0.99 | 2.7 | 1 | 1 | 0.1 | Carboxypeptidase N 83 kDa chain (Carboxypeptidase N regulatory subunit) |
| 35 | 4557417 | 1 | 22.1 | 5 | 6 | 0.67 | CD14 antigen precursor |
| 36 | 21361193 | 1 | 3 | 3 | 3 | 0.3 | CD44 antigen |
| 37 | 42761474 | 1 | 25 | 7 | 43 | 3.56 | CD59 antigen p18-20 |
| 38 | 4557485 | 1 | 4.9 | 4 | 4 | 0.4 | Ceruloplasmin |
| 39 | 4557443 | 0.57 | 3 | 1 | 1 | 0.06 | Cholesteryl ester transfer protein, plasma precursor |
| 40 | 42716297 | 1 | 16.5 | 8 | 8 | 0.72 | Clusterin isoform 1 |
| 41 | 4503635 | 0.99 | 4.3 | 1 | 2 | 0.24 | Coagulation factor II precursor |
| 42 | 15011913 | 1 | 10.3 | 9 | 10 | 0.99 | Collagen, type VI, alpha 1 precursor |
| 43 | 27262665 | 0.95 | 4.7 | 1 | 1 | 0.1 | Colony stimulating factor 1 isoform c precursor |
| 44 | 4557379 | 1 | 13.6 | 7 | 8 | 0.73 | Complement component 1 inhibitor precursor |
| 45 | 7706083 | 1 | 3.5 | 2 | 2 | 0.11 | Complement component 1, r subcomponent-like precursor |
| 46 | 23957690 | 0.97 | 2.7 | 2 | 2 | 0.13 | Component of oligomeric golgi complex 7 |
| 47 | 4557503 | 1 | 1.8 | 4 | 4 | 0.4 | Cubilin; intrinsic factor-cobalamin receptor |
| 48 | 4503107 | 0.99 | 11 | 1 | 2 | 0.2 | Cystatin C precursor |
| 49 | 21361254 | 1 | 14.2 | 4 | 6 | 0.47 | Deoxyribonuclease I |
| 50 | 19115954 | 0.77 | 0.4 | 2 | 3 | 0.08 | Dynein, axonemal, heavy polypeptide 5 |
| 51 | 9665262 | 1 | 4.9 | 2 | 3 | 0.3 | EGF-containing fibulin-like extracellular matrix protein 1 isoform a precursor; fibrillin-like |
| 52 | 13376091 | 0.97 | 1.3 | 1 | 1 | 0.1 | Elastin microfibril interfacer 3 |
| 53 | 34335272 | 1 | 26.1 | 6 | 9 | 0.98 | Endothelial protein C receptor precursor |
| 54 | 4503491 | 1 | 18.2 | 22 | 38 | 2.97 | Epidermal growth factor (beta-urogastrone) |
| 55 | 29789100 | 0.91 | 2.6 | 1 | 1 | 0.1 | Extracellular sulfatase SULF-2 |
| 56 | 24429586 | 0.96 | 3.8 | 1 | 1 | 0.11 | Fc fragment of IgG, low affinity III, receptor for (CD16) |
| 57 | 47132549 | 1 | 1.6 | 2 | 2 | 0.18 | Fibronectin 1 isoform 6 preproprotein |
| 58 | 19743803 | 0.99 | 2.7 | 1 | 2 | 0.2 | Fibulin 5 precursor |
| 59 | 8051586 | 0.99 | 5.1 | 1 | 1 | 0.1 | Ficolin 2 isoform b precursor |
| 60 | 4503747 | 0.99 | 0.5 | 1 | 1 | 0.1 | Filamin B, beta (actin binding protein 278) |
| 61 | 10834966 | 0.99 | 2.1 | 1 | 1 | 0.11 | Galactosidase, beta 1 |
| 62 | 5031863 | 1 | 16.1 | 9 | 17 | 1.4 | Galectin 3 binding protein |
| 63 | 4501887 | 1 | 6.9 | 2 | 2 | 0.2 | Gamma 1 Actin |
| 64 | 4503987 | 0.88 | 4.1 | 1 | 1 | 0.09 | Gamma-glutamyl hydrolase precursor |
| 65 | 38044288 | 1 | 6.8 | 6 | 21 | 1.67 | Gelsolin isoform b |
| 66 | 6912618 | 1 | 16.3 | 6 | 10 | 0.99 | Glutaminyl-peptide cyclotransferase precursor |
| 67 | 4504151 | 0.99 | 2.7 | 1 | 1 | 0.1 | Granulin |
| 68 | 4504349 | 1 | 15.6 | 2 | 2 | 0.19 | Hemoglobin beta chain |
| 69 | 11321561 | 1 | 4.8 | 2 | 2 | 0.2 | Hemopexin |
| 70 | 7427517 | 1 | 3 | 12 | 20 | 1.82 | Heparan sulfate proteoglycan 2; |
| 71 | 51471096 | 0.64 | 4.8 | 1 | 2 | 0.14 | Heterogeneous nuclear ribonucleoprotein A1 (Helix-destabilizing protein) |

TABLE 3-continued

| ID# | Protein gi Number | Protein Probability Score | Percent Coverage | Number of Unique Peptides | Total Number of Peptides | % Share of Spectrum ID's | Protein ID |
|---|---|---|---|---|---|---|---|
| 72 | 39930521 | 1 | 11.9 | 8 | 13 | 1.26 | Hypothetical protein BC013767 |
| 73 | 51468520 | 0.44 | 2.2 | 1 | 2 | 0.06 | Hypothetical protein DKFZp586O0120.1 —human (fragment) |
| 74 | 8923092 | 0.81 | 2.9 | 1 | 1 | 0.08 | Hypothetical protein FLJ20084 |
| 75 | 23503319 | 0.83 | 2.3 | 1 | 1 | 0.09 | Hypothetical protein MGC45378 |
| 76 | 4504579 | 1 | 4.5 | 2 | 3 | 0.14 | I factor (complement) |
| 77 | 51472926 | 0.99 | 8.9 | 1 | 3 | 0.3 | Ig heavy chain V-III region VH26 precursor, PREDICTED: similar to KIAA1501 protein |
| 78 | 51475407 | 1 | 14 | 3 | 4 | 0.4 | Ig kappa chain |
| 79 | 51460659 | 0.77 | 6 | 1 | 1 | 0.08 | Ig kappa variable region |
| 80 | 30795212 | 0.47 | 2.4 | 1 | 1 | 0.05 | IGF-II mRNA-binding protein 3; KH domain containing protein overexpressed in cancer |
| 81 | 21489959 | 0.99 | 6.3 | 1 | 1 | 0.11 | Immunoglobulin J chain |
| 82 | 5031809 | 0.99 | 3.3 | 1 | 1 | 0.1 | Immunoglobulin superfamily containing leucine-rich repeat |
| 83 | 16445029 | 0.96 | 1.6 | 1 | 3 | 0.2 | Immunoglobulin superfamily, member 8; CD81 partner 3 |
| 84 | 4504619 | 1 | 22.3 | 5 | 8 | 0.73 | Insulin-like growth factor binding protein 7 |
| 85 | 31542984 | 1 | 5.6 | 7 | 11 | 1.08 | Inter-alpha (globulin) inhibitor H4 (plasma Kallikrein-sensitive glycoprotein) |
| 86 | 4504875 | 1 | 10.3 | 2 | 6 | 0.61 | Kallikrein 1 preproprotein |
| 87 | 51470760 | 0.99 | 2.6 | 1 | 1 | 0.1 | KIAA0830 protein |
| 88 | 4504893 | 1 | 28.8 | 19 | 35 | 3.03 | Kininogen 1 |
| 89 | 5803023 | 1 | 15.7 | 8 | 11 | 1.07 | Lectin, mannose-binding 2 |
| 90 | 16418467 | 1 | 5.2 | 2 | 3 | 0.19 | Leucine-rich alpha-2-glycoprotein 1 |
| 91 | 14150145 | 1 | 9.5 | 4 | 4 | 0.4 | Limitrin |
| 92 | 10835248 | 1 | 10.2 | 2 | 2 | 0.15 | Lithostathine 1 beta |
| 93 | 21264363 | 1 | 30.8 | 6 | 19 | 1.59 | Mannan-binding lectin serine protease 2 isoform 1 precursor |
| 94 | 24497519 | 1 | 4.3 | 2 | 2 | 0.21 | Mannosidase, alpha, class 1A, member 1 |
| 95 | 4503001 | 0.48 | 2.4 | 1 | 1 | 0.05 | Mast cell carboxypeptidase A3 precursor |
| 96 | 13699834 | 0.99 | 3.6 | 1 | 1 | 0.1 | Matrilin 4 isoform 3 precursor |
| 97 | 6806919 | 1 | 1 | 5 | 5 | 0.47 | Megalin |
| 98 | 4502095 | 1 | 2.7 | 2 | 2 | 0.16 | Membrane alanine aminopeptidase |
| 99 | 20270317 | 0.49 | 3.4 | 1 | 1 | 0.05 | Mitochondrial ribosome recycling factor isoform 1 |
| 100 | 4505395 | 0.98 | 0.8 | 1 | 3 | 0.2 | Nidogen (enactin) |
| 101 | 5031985 | 1 | 22.8 | 3 | 4 | 0.22 | Nuclear transport factor 2; placental protein 15 |
| 102 | 9257232 | 1 | 22.9 | 4 | 4 | 0.36 | Orosomucoid-1 (alpha-1-acid glycoprotein-1) |
| 103 | 23943854 | 0.93 | 4.9 | 2 | 2 | 0.16 | Pepsinogen A5 |
| 104 | 4827036 | 1 | 19.9 | 4 | 5 | 0.4 | Peptidoglycan recognition protein 1; TNF superfamily, member 3 (LTB)-like (peptidoglycan recognition protein) |
| 105 | 21361845 | 1 | 4.6 | 2 | 2 | 0.19 | Peptidoglycan recognition protein L precursor |
| 106 | 4505621 | 1 | 18.2 | 2 | 2 | 0.2 | Phosphatidylethanolamine binding protein |
| 107 | 7110641 | 0.68 | 2.7 | 1 | 1 | 0.07 | Phospholipase D3 |
| 108 | 6006001 | 0.92 | 5.3 | 1 | 1 | 0.1 | Plasma glutathione peroxidase 3 precursor |
| 109 | 4505881 | 1 | 5.6 | 3 | 4 | 0.4 | Plasminogen |
| 110 | 4505863 | 0.99 | 2.3 | 2 | 2 | 0.14 | Plasminogen activator, urokinase |
| 111 | 19923372 | 0.71 | 4.8 | 2 | 2 | 0.09 | Polio virus receptor; ortholog of mouse Tage4 |
| 112 | 31377806 | 1 | 6.8 | 5 | 7 | 0.43 | Polymeric immunoglobulin receptor; hepatocellular carcinoma associated protein TB6 |
| 113 | 51473011 | 1 | 32.8 | 2 | 2 | 0.18 | Polyubiquitin B |
| 114 | 4505959 | 0.71 | 1.9 | 1 | 3 | 0.11 | POU domain, class 2, transcription factor 2 |
| 115 | 4505821 | 1 | 21.2 | 2 | 2 | 0.21 | Prolactin-induced protein |
| 116 | 4557833 | 0.91 | 2 | 1 | 9 | 0.25 | Propionyl-Coenzyme A carboxylase, alpha polypeptide precursor |
| 117 | 11386147 | 0.98 | 2.9 | 1 | 1 | 0.11 | Prosaposin (sphingolipid activator protein-1) |
| 118 | 32171249 | 1 | 27.9 | 7 | 13 | 1.08 | Prostaglandin D2 synthase 21 kDa |
| 119 | 4506153 | 0.99 | 4.1 | 1 | 1 | 0.1 | Prostasin preproprotein |
| 120 | 4502173 | 1 | 11.9 | 2 | 2 | 0.21 | Prostate specific antigen isoform 1 preproprotein |
| 121 | 6382064 | 1 | 19.2 | 7 | 8 | 0.79 | Prostatic acid phosphatase precursor |
| 122 | 4506121 | 1 | 11.8 | 3 | 5 | 0.5 | Protein Z, vitamin K-dependent plasma glycoprotein |
| 123 | 5803139 | 0.76 | 10.6 | 2 | 2 | 0.11 | RBP4 gene product |
| 124 | 9966777 | 0.97 | 10.2 | 1 | 1 | 0.11 | Resistin; found in inflammatory zone 3 |
| 125 | 51464234 | 0.9 | 1 | 2 | 2 | 0.12 | Rho GTPase activating protein 10 |
| 126 | 4506549 | 0.66 | 9.3 | 1 | 1 | 0.07 | Ribonuclease, RNase A family, 2 (eosinophil-derived neurotoxin) |
| 127 | 17511435 | 1 | 6.4 | 4 | 4 | 0.38 | Roundabout homolog 4, magic roundabout |
| 128 | 4506773 | 0.99 | 13.2 | 1 | 1 | 0.1 | S100 calcium-binding protein A9; calgranulin B; S100 calcium-binding protein A9 (calgranulin B) |
| 129 | 4506869 | 0.99 | 6.5 | 1 | 1 | 0.11 | Secreted and transmembrane 1 precursor |
| 130 | 4759166 | 1 | 18.3 | 6 | 14 | 1.37 | Secreted phosphoprotein 1 (osteopontin) |
| 131 | 32698964 | 1 | 23.3 | 3 | 7 | 0.54 | Secretory protein LOC284013 |
| 132 | 21361198 | 1 | 24.6 | 11 | 22 | 1.67 | Serine (or cysteine) proteinase inhibitor, clade A member 1 |
| 133 | 21361195 | 1 | 22.4 | 7 | 11 | 1.13 | Serine (or cysteine) proteinase inhibitor, clade A member 2 |
| 134 | 22027518 | 0.75 | 2.1 | 1 | 1 | 0.08 | Serine carboxypeptidase vitellogenic-like |
| 135 | 13775198 | 0.99 | 16.1 | 1 | 1 | 0.1 | SH3 domain binding glutamic acid-rich protein like 3 |
| 136 | 21687060 | 0.82 | 4.7 | 1 | 1 | 0.08 | Similar to common salivary protein 1 |
| 137 | 41150478 | 0.88 | 7.2 | 1 | 1 | 0.09 | Similar to immunoglobulin M chain |
| 138 | 7019521 | 0.64 | 1.8 | 1 | 1 | 0.07 | Squamous cell carcinoma antigen recognized by T cells 2 |
| 139 | 38202250 | 0.85 | 6.4 | 2 | 2 | 0.12 | Sulfatase modifying factor 1; C-alpha-formylglycine-generating enzyme |

TABLE 3-continued

| ID# | Protein gi Number | Protein Probability Score | Percent Coverage | Number of Unique Peptides | Total Number of Peptides | % Share of Spectrum ID's | Protein ID |
|---|---|---|---|---|---|---|---|
| 140 | 4507151 | 1 | 16.7 | 4 | 4 | 0.36 | Superoxide dismutase 3, extracellular |
| 141 | 10092665 | 0.82 | 1.2 | 1 | 1 | 0.08 | Sushi domain containing 2 |
| 142 | 4507557 | 1 | 19.8 | 5 | 6 | 0.58 | Tetranectin (plasminogen binding protein) |
| 143 | 11641299 | 0.56 | 4 | 1 | 1 | 0.06 | Torsin family 3, member A; ATP-dependant interferon response protein 1 |
| 144 | 4557871 | 1 | 25.6 | 15 | 17 | 1.65 | Transferrin |
| 145 | 7305595 | 0.49 | 1.7 | 1 | 1 | 0.05 | Transportin 2 |
| 146 | 4507725 | 0.99 | 8.8 | 1 | 1 | 0.11 | Transthyretin |
| 147 | 4885629 | 1 | 21.7 | 2 | 2 | 0.2 | Trefoil factor 2 precursor |
| 148 | 23308722 | 0.84 | 1.3 | 1 | 1 | 0.08 | TTK protein kinase |
| 149 | 9966885 | 1 | 9.4 | 5 | 7 | 0.63 | Tumor endothelial marker 1 precursor; endosialin |
| 150 | 4759246 | 0.85 | 4.7 | 1 | 3 | 0.18 | Tumor necrosis factor receptor superfamily, member 18 isoform 1 precursor |
| 151 | 4507833 | 1 | 22 | 25 | 63 | 5.65 | Uromodulin; Tamm-Horsfall glycoprotein |
| 152 | 4507809 | 1 | 12.1 | 2 | 3 | 0.26 | Uteroglobin |
| 153 | 15619010 | 0.47 | 0.3 | 1 | 1 | 0.05 | Vacuolar protein sorting 13A isoform A |
| 154 | 4507875 | 0.89 | 1.7 | 1 | 1 | 0.09 | Vascular cell adhesion molecule 1 isoform a precursor |
| 155 | 18201911 | 1 | 5.6 | 2 | 2 | 0.22 | Vitronectin precursor |

REFERENCES

The references listed below as well as all references cited in the specification are incorporated herein by reference to the extent that they supplement, explain, provide a background for or teach methodology, techniques and/or compositions employed herein.

Anderson N L, Hunter C L., *Mol Cell Proteomics*. 2005 Dec. 6; [Epub ahead of print] Quantitative mass spectrometric MRM assays for major plasma proteins.

Bartels, *Biomed. Environ. Mass Spectrom.* 1990 19, 363-368.

Berhane B T, Zong C, Liem D A, Huang A, Le S, Edmondson R D, Jones R C, Qiao X, Whitelegge J P, Ping P, Vondriska T M, *Proteomics*. 2005 August; 5(13):3520-30. Cardiovascular-related proteins identified in human plasma by the HUPO Plasma Proteome Project pilot phase.

Biemann, K. (1990) Sequencing of peptides by tandem mass spectrometry and high-energy collision-induced dissociation. Methods Enzymol. 193, 455-479.

Caby M P, Lankar D, Vincendeau-Scherrer C, Raposo G, Bonnerot C., *Int Immunol.* 2005 July; 17(7):879-87. Exosomal-like vesicles are present in human blood plasma.

Clauser, P. Baker and A. L. Burlingame, in Proceedings of the 44th ASMS Conference of *Mass Spectrometry* and Allied Topics. Portland, Oreg., 1996, pp. 365-366.

Echan L A, Tang H Y, Ali-Khan N, Lee K, Speicher D W., *Proteomics*. 2005 August; 5(13):3292-303. Depletion of multiple high-abundance proteins improves protein profiling capacities of human serum and plasma.

Fernandez-de-Cossjo, J. et al., (1995) CABIOS 11, 427-434.

Gatti J L, Metayer S, Belghazi M, Dacheux F, Dacheux J L., *Biol Reprod.* 2005 June; 72(6):1452-65. Identification, proteomic profiling, and origin of ram epididymal fluid exosome-like vesicles. gentamicin-induced nephrotoxicity in the rat.

Greenough C, Jenkins R E, Kitteringham N R, Pirmohamed M, Park B K, Pennington S R., *Proteomics*. 2004 October; 4(10):3107-11. A method for the rapid depletion of albumin and immunoglobulin from human plasma.

Haubitz M, Wittke S, Weissinger E M, Walden M, Rupprecht H D, Floege J, Haller H, Mischak H., *Kidney Int.* 2005 June; 67(6):2313-20. Urine protein patterns can serve as diagnostic tools in patients with IgA nephropathy.

Hegmans J P, Bard M P, Hemmes A, Luider T M, Kleijmeer M J, Prins J B, Zitvogel L, Burgers S A, Hoogsteden H C, Lambrecht B N., *Am J. Pathol.* 2004 May; 164(5):1807-15. Proteomic analysis of exosomes secreted by human mesothelioma cells.

Hines, A. et al. *J. Am. Soc. Mass Spectrom.* 1995 3, 326-336.

Ishikawa et al. *Biomed. Environ. Mass Spectrom.* 1986 13, 373-380.

Johnson et al. *Biomed. Environ. Mass Spectrom.* 1989 18, 945-957.

Knapp, J. *Am. Soc. Mass Spectrom.* 1995 6, 947-961.

Lenz E M, Bright J, Knight R, Westwood F R, Davies D, Major H, Wilson I D., *Biomarkers*. 2005 March-June; 10(2-3):173-87. Metabonomics with 1H-NMR spectroscopy and liquid chromatography-mass spectrometry applied to the investigation of metabolic changes caused by Mallegol J, van Niel G, Heyman M., *Blood Cells Mol. Dis.* 2005 July-August; 35(1):11-6. Phenotypic and functional characterization of intestinal epithelial exosomes.

Mann and Wilm *Anal Chem.* 1994 66, 4390.

Mortz, E. et al. *PNAS* 1996 93, 8264.

Papayannopoulos, I. A. *Mass Spectrometry Reviews* 1995 14, 49-73.

PCT International Patent Application No. WO99/03499.

Pisitkun T, Shen R F, Knepper M A., *Proc Natl Acad Sci USA*. 2004 Sep. 7; 101(36):13368-73. Identification and proteomic profiling of exosomes in human urine.

Shevchenko et al. *J. of Protein Chemistry* 1997 16(5):481-90.

Siegel et al. *Biomed. Environ. Mass Spectrom.* 1988 15, 333-343.

Snyder S, Pendergraph B., *Am Fam Physician*. 2005 Nov. 1; 72(9):1723-32. Detection and evaluation of chronic kidney disease.

Thongboonkerd V, McLeish K R, Arthur J M, Klein J B., *Kidney Int.* 2002 October; 62(4):1461-9. Proteomic analysis of normal human urinary proteins isolated by acetone precipitation or ultracentrifugation.

U.S. Pat. No. 5,538,897.

van Niel G, Raposo G, Candalh C, Boussac M, Hershberg R, Cerf-Bensussan N, Heyman M., *Gastroenterology*. 2001 August; 121(2):337-49. Intestinal epithelial cells secrete exosome-like vesicles.

Veenstra T D, Conrads T P, Hood B L, Avellino A M, Ellenbogen R G, Morrison R S., *Mol Cell Proteomics*. 2005 April; 4(4):409-18. Epub 2005 Jan. 31. Biomarkers: mining the biofluid proteome.

Vidal B C, Bonventre J V, I-Hong Hsu S., *Clin Sci* (Lond). 2005 November; 109(5):421-30. Towards the application of proteomics in renal disease diagnosis.

Yates III, P. R. Griffin and L. E. Hood, in Techniques in Protein Chemistry, edited by J. J. Villafranca, Vol. 2, Academic Press, San Diego pp. 477-485 (1991).

Zhao R., Clin Lab Sci. 2005 Fall; 18(4):254-62. From single cell gene-based diagnostics to diagnostic genomics: current applications and future perspectives.

Zhou M, Lucas D A, Chan K C, Issaq H J, Petricoin E F 3rd, Liotta L A, Veenstra T D, Conrads T P., *Electrophoresis*. 2004 May; 25(9):1289-98. An investigation into the human serum "interactome".

Zidarov et al. (1990) Biomed, Environ. Mass Spectrom. 19(1), 13-26.

It will be understood that various details of the presently disclosed subject matter may be changed without departing from the scope of the disclosed subject matter. Furthermore, the foregoing description is for the purpose of illustration only, and not for the purpose of limitation.

What is claimed is:

1. A method of isolating exosomes from a biological fluid sample, the method comprising:
   (a) receiving an uncultured biological fluid sample from a subject, the biological fluid sample comprising exosomes;
   (b) filtering the biological fluid sample directly through a filtration module comprising a filter having an average pore diameter of between about 0.01 µm and about 0.15 µm and having a hydrophilic surface to reduce protein adsorption to the surface of the filter; and
   (c) collecting from the filtration module a retentate comprising the exosomes, thereby isolating the exosomes from the biological fluid sample.

2. The method of claim 1, wherein the biological fluid sample provided is a clarified biological fluid sample.

3. The method of claim 2, wherein the biological fluid sample is clarified by low-speed centrifugation and collection of a supernatant comprising the clarified biological fluid sample.

4. The method of claim 3, wherein the biological fluid sample is centrifuged at about 3,000×g or less.

5. The method of claim 1, wherein the biological fluid sample is selected from the group consisting of blood, blood plasma, and urine.

6. The method of claim 5, wherein the biological fluid sample is urine.

7. The method of claim 6, wherein the urine has been treated with a protease inhibitor.

8. The method of claim 6, wherein the urine has been previously frozen.

9. The method of claim 1, wherein the exosomes are urinary exosomes.

10. The method of claim 1, wherein the filtration module is a fiber-based filtration cartridge.

11. The method of claim 10, wherein the filter comprises polypropylene hollow fibers.

12. The method of claim 1, wherein the filtration module is a membrane filtration module.

13. The method of claim 12, wherein the filter is a filtration disc comprising hydrophilic polyvinylidene difluoride.

14. The method of claim 1, wherein the filter has an average pore diameter of about 0.1 µm.

15. The method of claim 1, wherein the filter comprises a material selected from the group consisting of polypropylene, polyvinylidene difluoride, polyethylene, polyfluoroethylene, cellulose, secondary cellulose acetate, polysulfone, polyethersulfone, polyvinylalcohol and ethylenevinyl alcohol.

16. The method of claim 1, wherein the retentate comprising the exosomes is collected by washing the retentate from the filtration module.

17. The method of claim 1, wherein the collected retentate comprising the exosomes is resuspended in a buffer solution.

18. A method of identifying biomarker polypeptides, quantitating biomarker polypeptides, or both in a biological fluid sample, the method comprising:
   (a) receiving an uncultured biological fluid sample from a subject, the biological fluid sample comprising exosomes, wherein the exosomes comprise biomarker polypeptides;
   (b) filtering the biological fluid sample directly through a filtration module comprising a filter having an average pore diameter of between about 0.01 µm and about 0.15 µm and having a hydrophilic surface to reduce protein adsorption to the surface of the filter;
   (c) collecting from the filtration module a retentate comprising the exosomes;
   (d) isolating the biomarker polypeptides from the exosomes; and
   (e) identifying, quantitating, or both the isolated biomarker polypeptides.

19. The method of claim 18, wherein the biological fluid sample provided is a clarified biological fluid sample.

20. The method of claim 19, wherein the biological fluid sample is clarified by low-speed centrifugation and collection of a supernatant comprising the clarified biological fluid sample.

21. The method of claim 20, wherein the biological fluid sample is centrifuged at about 3,000×g or less.

22. The method of claim 18, wherein the biological fluid sample is selected from the group consisting of blood, blood plasma, and urine.

23. The method of claim 22, wherein the biological fluid sample is urine.

24. The method of claim 23, wherein the urine has been treated with a protease inhibitor.

25. The method of claim 23, wherein the urine has been previously frozen.

26. The method of claim 18, wherein the exosomes are urinary exosomes.

27. The method of claim 18, wherein the filtration module is a fiber-based filtration cartridge.

28. The method of claim 27, wherein the filter comprises polypropylene hollow fibers.

29. The method of claim 18, wherein the filtration module is a membrane filtration module.

30. The method of claim 29, wherein the filter is a filtration disc comprising hydrophilic polyvinylidene difluoride.

31. The method of claim 18, wherein the filter has an average pore diameter of about 0.1 µm.

32. The method of claim 18, wherein the filter comprises a material selected from the group consisting of polypropylene, polyvinylidene difluoride, polyethylene, polyfluoroethylene, cellulose, secondary cellulose acetate, polysulfone, polyethersulfone, polyvinylalcohol, and ethylenevinyl alcohol.

33. The method of claim 18, wherein the retentate comprising the exosomes is collected by washing the retentate from the filtration module.

34. The method of claim 18, wherein the collected retentate comprising the exosomes is resuspended in a buffer solution.

35. The method of claim 18, wherein the biomarker peptides are identified, quantitated, or both by immunoassay, mass spectrometry, or both.

36. The method of claim 35, wherein the mass spectrometry is matrix-assisted laser desorption ionization time-of-flight mass spectrometry (MALDI MS).

37. The method of claim 35, wherein the immunoassay is selected from the group consisting of Western blot, enzyme-linked immunoassay (ELISA), radioimmunoassay (RIA), and competitive binding assay.

38. A method of isolating exosome biomarker polypeptides from a biological fluid sample, the method comprising:
   (a) receiving an uncultured biological fluid sample from a subject, the biological fluid sample comprising exosomes, wherein the exosomes comprise biomarker polypeptides;
   (b) filtering the biological fluid sample directly through a filtration module comprising a filter having an average pore diameter of between about 0.01 µm and about 0.15 µm and having a hydrophilic surface to reduce protein adsorption to the surface of the filter;
   (c) collecting from the filtration module a retentate comprising the exosomes; and
   (d) isolating the biomarker polypeptides from the exosomes.

39. The method of claim 38, wherein the biological fluid sample provided is a clarified biological fluid sample.

40. The method of claim 39, wherein the biological fluid sample is clarified by low-speed centrifugation and collection of a supernatant comprising the clarified biological fluid sample.

41. The method of claim 40, wherein the biological fluid sample is centrifuged at about 3,000×g or less.

42. The method of claim 38, wherein the biological fluid sample is selected from the group consisting of blood, blood plasma, and urine.

43. The method of claim 42, wherein the biological fluid sample is urine.

44. The method of claim 43, wherein the urine has been treated with a protease inhibitor.

45. The method of claim 43, wherein the urine has been previously frozen.

46. The method of claim 38, wherein the exosomes are urinary exosomes.

47. The method of claim 38, wherein the filtration module is a fiber-based filtration cartridge.

48. The method of claim 47, wherein the filter comprises polypropylene hollow fibers.

49. The method of claim 38, wherein the filtration module is a membrane filtration module.

50. The method of claim 49, wherein the filter is a filtration disc comprising hydrophilic polyvinylidene difluoride.

51. The method of claim 38, wherein the filter has an average pore diameter of about 0.1 µm.

52. The method of claim 38, wherein the filter comprises a material selected from the group consisting of polypropylene, polyvinylidene difluoride, polyethylene, polyfluoroethylene, cellulose, secondary cellulose acetate, polysulfone, polyethersulfone, polyvinylalcohol, and ethylenevinyl alcohol.

53. The method of claim 38, wherein the retentate comprising the exosomes is collected by washing the retentate from the filtration module.

54. The method of claim 38, wherein the collected retentate comprising the exosomes is resuspended in a buffer solution.

55. The method of claim 38, wherein the biomarker peptides are isolated by electrophoretic separation, immunoisolation, chromatography, or combinations thereof.

56. A method of diagnosing a disorder or measuring a disorder state in a subject, the method comprising:
   (a) receiving an uncultured biological fluid sample from a subject, the biological fluid sample comprising exosomes, wherein the exosomes comprise biomarker polypeptides;
   (b) filtering the biological fluid sample through a filtration module comprising a filter having an average pore diameter of between about 0.01 µm and about 0.15 µm and having a hydrophilic surface to reduce protein adsorption to the surface of the filter;
   (c) collecting from the filtration module a retentate comprising the exosomes;
   (d) isolating the biomarker polypeptides from the exosomes;
   (e) identifying, quantitating, or both the isolated biomarker polypeptides; and
   (f) diagnosing the presence of the disorder or measuring the disorder state in the subject based on the identified and/or quantitated biomarker polypeptides.

57. The method of claim 56, wherein the biological fluid sample provided is a clarified biological fluid sample.

58. The method of claim 57, wherein the biological fluid sample is clarified by low-speed centrifugation and collection of a supernatant comprising the clarified biological fluid sample.

59. The method of claim 58, wherein the biological fluid sample is centrifuged at about 3,000×g or less.

60. The method of claim 56, wherein the biological fluid sample is selected from the group consisting of blood, blood plasma, and urine.

61. The method of claim 60, wherein the biological fluid sample is urine.

62. The method of claim 61, wherein the urine has been treated with a protease inhibitor.

63. The method of claim 61, wherein the urine has been previously frozen.

64. The method of claim 56, wherein the exosomes are urinary exosomes.

65. The method of claim 56, wherein the filtration module is a fiber-based filtration cartridge.

66. The method of claim 65, wherein the filter comprises polypropylene hollow fibers.

67. The method of claim 56, wherein the filtration module is a membrane filtration module.

68. The method of claim 67, wherein the filter is a filtration disc comprising hydrophilic polyvinylidene difluoride.

69. The method of claim 56, wherein the filter has an average pore diameter of about 0.1 µm.

70. The method of claim 56, wherein the filter comprises a material selected from the group consisting of polypropylene, polyvinylidene difluoride, polyethylene, polyfluoroethylene, cellulose, secondary cellulose acetate, polysulfone, polyethersulfone, polyvinylalcohol, and ethylenevinyl alcohol.

71. The method of claim 56, wherein the retentate comprising the exosomes is collected by washing the retentate from the filtration module.

72. The method of claim 56, wherein the collected retentate comprising the exosomes is resuspended in a buffer solution.

73. The method of claim 56, wherein the biomarker peptides are identified, quantitated, or both by immunoassay, mass spectrometry, or both.

74. The method of claim 73, wherein the mass spectrometry is matrix-assisted laser desorption ionization time-of-flight mass spectrometry (MALDI MS).

75. The method of claim 73, wherein the immunoassay is selected from the group consisting of Western blot, enzyme-linked immunoassay (ELISA), radioimmunoassay (RIA), and competitive binding assay.

76. The method of claim 56, wherein the disorder is selected from the group consisting of diabetes, water-balance disorders, acute kidney injury, glomerulonephritis, drug-induced acute renal failure and allergy, acute and chronic kidney transplant rejection, inherited renal diseases, myocardial ischemia, cardiovascular risk, prostatic hypertrophy and prostatic cancer, systemic lupus erythematosus, and rheumatoid arthritis.

* * * * *